United States Patent
Li et al.

(10) Patent No.: US 10,071,994 B2
(45) Date of Patent: Sep. 11, 2018

(54) N-SULFONYL HOMOSERINE LACTONE DERIVATIVES, PREPARATION METHOD AND USE THEREOF

(71) Applicant: Institute of Pharmacology and Toxicology Academy of Military Medical Sciences P.L.A. China, Beijing (CN)

(72) Inventors: Song Li, Beijing (CN); Junhai Xiao, Beijing (CN); Qi Sun, Beijing (CN); Wu Zhong, Beijing (CN); Lili Wang, Beijing (CN); Zhibing Zheng, Beijing (CN); Yunde Xie, Beijing (CN); Xingzhou Li, Beijing (CN); Xinbo Zhou, Beijing (CN); Xiaokui Wang, Beijing (CN); Ruiyuan Cao, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 76 days.

(21) Appl. No.: 15/314,888

(22) PCT Filed: May 25, 2015

(86) PCT No.: PCT/CN2015/079673
§ 371 (c)(1),
(2) Date: Nov. 29, 2016

(87) PCT Pub. No.: WO2015/180597
PCT Pub. Date: Dec. 3, 2015

(65) Prior Publication Data
US 2018/0179193 A1  Jun. 28, 2018

(30) Foreign Application Priority Data
May 30, 2014 (CN) .......................... 2014 1 0238384

(51) Int. Cl.
| | | |
|---|---|---|
| *C07D 307/33* | (2006.01) | |
| *A61K 31/341* | (2006.01) | |
| *C07D 409/12* | (2006.01) | |
| *A61K 31/381* | (2006.01) | |
| *A61K 45/06* | (2006.01) | |
| *C07D 407/12* | (2006.01) | |
| *C12Q 1/02* | (2006.01) | |
| *C07D 405/12* | (2006.01) | |
| *A61K 31/4025* | (2006.01) | |
| *A61K 31/365* | (2006.01) | |

(52) U.S. Cl.
CPC .......... *C07D 409/12* (2013.01); *A61K 31/365* (2013.01); *A61K 31/381* (2013.01); *A61K 31/4025* (2013.01); *A61K 45/06* (2013.01); *C07D 307/33* (2013.01); *C07D 405/12* (2013.01); *C07D 407/12* (2013.01); *C12Q 1/025* (2013.01)

(58) Field of Classification Search
None
See application file for complete search history.

(56) References Cited

FOREIGN PATENT DOCUMENTS

| | | |
|---|---|---|
| EP | 2 955 174 A1 | 12/2015 |
| JP | 2002-105073 A | 4/2002 |
| WO | WO 03/106445 A1 | 12/2003 |

OTHER PUBLICATIONS

International Search Report (ISR) for PCT/CN2015/079673; I.A. fd: May 25, 2015, dated Aug. 10, 2015, State Intellectual Property Office of the P.R. China, Beijing, China.
International Preliminary Report on Patentability (IPRP) including the Written Opinion of the International Searching Authority (PCT Rule 44bis) for PCT/CN2015/079673; I.A. fd: May 25, 2015, dated Dec. 6, 2016, by the International Bureau of WIPO, Geneva, Switzerland.
Zhao, M. et al., "Design, synthesis and biological evaluation of N-sulfonyl homoserine lactone derivatives as inhibitors of quorum sensing in *Chromobacterium violaceum*," Molecules. Mar. 13, 2013;18(3):3266-78. doi: 10.3390/molecules18033266, MDPI, Basel, Switzerland.
Extended European search report including the supplementary European search report and the European search opinion, dated Dec. 15, 2017, for EP Appl. No. 15798935.1, European Patent Office, Munich, Germany.
Castang, S et al., "N-Sulfonyl homoserine lactones as antagonists of bacterial quorum sensing," Bioorg Med Chem Lett. Oct. 18, 2004;14(20):5145-9, Elsevier Science Direct, Oxford, England.

*Primary Examiner* — Zinna Northington Davis
(74) *Attorney, Agent, or Firm* — Sterne, Kessler, Goldstein & Fox P.L.L.C.

(57) ABSTRACT

The invention relates to a homoserine lactone derivative of Formula I, preparation method and use thereof. The compound has an effect of regulatory of bacterial quorum sensing, and is useful for preventing and/or treating a disease caused by infection of a bacterium

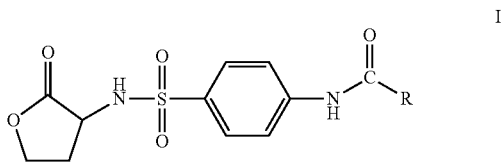

I

20 Claims, No Drawings

N-SULFONYL HOMOSERINE LACTONE DERIVATIVES, PREPARATION METHOD AND USE THEREOF

TECHNICAL FIELD

The invention belongs to medical and chemical engineering field, specifically relates to N-sulfonyl homoserine lactone derivatives, preparation method thereof, and use thereof in the manufacture of a medicament for the prevention and/or treatment of a disease caused by a Gram-negative bacterium.

BACKGROUND ART

During the growth of bacterial quorum, bacteria can generate chemical signaling molecules (also called auto inducers) ceaselessly and these signaling molecules are subsequently secreted in the extracellular environment. When the concentration of the signaling molecules reaches a threshold, the expression of relevant genes in bacteria, such as genes related with bioluminescence, formation of biofilms and virulence, is regulated or activated to adapt to the environmental changes. Such a regulatory system is known as bacterial quorum sensing (QS) system.

QS system was first observed in *V. fischeri*. When the density of bacteria was high, the bacteria luminesce so as to catch food, avoid predators, etc. It is found by studying on its mechanism that, in *V. fischeri*, N-acyl homoserine lactones (AHL) synthesized by Luxi protein can bind to N-terminal of AHL receptor protein encoded by LuxR and form a specific configuration to enable the binding of C-terminal of AHL receptor protein to the target DNA sequence, thereby activating the transcription and expression of illuminant gene. Similar regulatory systems were found in many Gram-positive or Gram-negative bacteria. Their mechanism resides in that when bacteria are at a low population density, little autoinducer is produced, the inducer is diffused extracellularly and diluted immediately in the surrounding environment. When the population density of bacteria increases gradually and reaches a threshold, the signaling molecules will permeate into cells and bind to the corresponding transcriptional regulatory protein to form a transcriptional regulatory protein-signaling molecule polymer, which can bind to a specific DNA sequence encoding the signaling molecule in chromosome and enables the expression of relevant target gene, resulting in the production of more signaling molecules. Such communication and transduction of information among bacteria have been proposed for a long time. However, systematic research is only conducted in the recent 10 years. Such a phenomenon has been demonstrated in many bacteria now.

In the late 1970s, scientists found that naturally occurring or artificially synthesized bacterial quorum-sensing regulators (including agonists or inhibitors) can interfere with the transduction of signaling system and regulate the expression of virulence gene in bacteria. Bacterial quorum-sensing regulators deprive pathogenic bacteria of pathogenic ability by regulating the expression of its virulence gene, without interfering with normal physiological functions of cells in vivo, thus are regarded as a new direction for the development of antibacterials. Bacterial quorum-sensing inhibitors can be used in combination with antibiotics to enhance sensitivity of pathogenic bacteria to antibiotics so as to improve therapeutic effect of drugs, and can be used to treat various diseases caused by Gram-negative bacteria such as endocarditis, peritonitis, gastroenteritis, cholecystitis, cystitis, diarrhea, pyothorax, and sepsis.

The object of the invention is to find out new bacterial quorum-sensing regulators for use in the prevention and/or treatment of a disease caused by a Gram-negative bacterium, particularly a disease caused by a drug-resistant Gram-negative bacterium.

CONTENTS OF INVENTION

In the first aspect, the invention provides a homoserine lactone derivative of Formula I, or a racemate or optical isomer, pharmaceutically acceptable salt, solvate, or hydrate thereof,

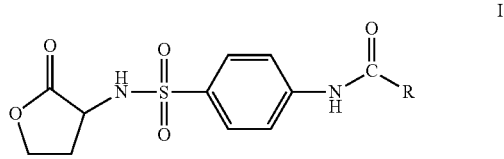

wherein, R is a group selected from heteroaryl and benzyl, optionally the group is mono-substituted or multi-substituted (e.g., di-substituted or tri-substituted) by a substituent selected from a group consisting of: halogen, trifluoromethyl, nitro, and $C_{1-6}$ alkyl.

For the homoserine lactone derivative, or a racemate or optical isomer, pharmaceutically acceptable salt, solvate, or hydrate thereof according to the first aspect of the invention, preferably R is a group selected from thienyl, furyl, pyrrolyl, pyridyl and benzyl, optionally the group is mono-substituted or multi-substituted (e.g., di-substituted or tri-substituted) by a substituent selected from halogen, trifluoromethyl, nitro, and $C_{1-6}$ alkyl.

In some embodiments of the invention, R is thienyl, optionally said thienyl is mono-substituted by a substituent selected from halogen, nitro, and $C_{1-6}$ alkyl.

In some embodiments of the invention, R is furyl, optionally said fury is mono-substituted by a substituent selected from halogen, nitro, and $C_{1-6}$ alkyl, or di-substituted by halogen.

In some embodiments of the invention, R is pyrrolyl.

In some embodiments of the invention, R is pyridyl.

In some embodiments of the invention, R is benzyl, optionally said benzyl is mono-substituted by a substituent selected from halogen, nitro, $C_{1-6}$ alkyl and trifluoromethyl, or di-substituted by halogen.

For the homoserine lactone derivative, or a racemate or optical isomer, pharmaceutically acceptable salt, solvate, or hydrate thereof according to the first aspect of the invention, preferably R is selected from the group consisting of thienyl, chlorothienyl, bromothienyl, nitrothienyl, methylthienyl, furyl, nitrofuryl, bromofuryl, methylfuryl, dibromofuryl, pyrrolyl, pyridyl, chloropyridyl, fluorobenzyl, chlorobenzyl, bromobenzyl, methylbenzyl, trifluoromethylbenzyl, nitrobenzyl, and dichlorobenzyl.

For the homoserine lactone derivative, or a racemate or optical isomer, pharmaceutically acceptable salt, solvate, or hydrate thereof according to the first aspect of the invention, preferably the homoserine lactone derivative is selected from:

(S)—N-(4-(N-(2-oxotetrahydrofuran-3-yl)sulfamoyl)phenyl)thiophene-2-carboxamide (Compound 1);

(S)—N-(4-(N-(2-oxotetrahydrofuran-3-yl)sulfamoyl)phenyl)thiophene-3-carboxamide (Compound 2);
(S)-5-chloro-N-(4-(N-(2-oxotetrahydrofuran-3-yl)sulfamoyl)phenyl)thiophene-2-carboxamide (Compound 3);
(S)-5-bromo-N-(4-(N-(2-oxotetrahydrofuran-3-yl)sulfamoyl)phenyl)thiophene-2-carboxamide (Compound 4);
(S)-5-nitro-N-(4-(N-(2-oxotetrahydrofuran-3-yl)sulfamoyl)phenyl)thiophene-2-carboxamide (Compound 5);
(S)-4-bromo-N-(4-(N-(2-oxotetrahydrofuran-3-yl)sulfamoyl)phenyl)thiophene-2-carboxamide (Compound 6);
(S)-4-methyl-N-(4-(N-(2-oxotetrahydrofuran-3-yl)sulfamoyl)phenyl)thiophene-2-carboxamide (Compound 7);
(S)-3-methyl-N-(4-(N-(2-oxotetrahydrofuran-3-yl)sulfamoyl)phenyl)thiophene-2-carboxamide (Compound 8);
(S)-3-chloro-N-(4-(N-(2-oxotetrahydrofuran-3-yl)sulfamoyl)phenyl)thiophene-2-carboxamide (Compound 9);
(S)-3-bromo-N-(4-(N-(2-oxotetrahydrofuran-3-yl)sulfamoyl)phenyl)thiophene-2-carboxamide (Compound 10);
(S)—N-(4-(N-(2-oxotetrahydrofuran-3-yl)sulfamoyl)phenyl)furan-2-carboxamide (Compound 11);
(S)—N-(4-(N-(2-oxotetrahydrofuran-3-yl)sulfamoyl)phenyl)furan-3-carboxamide (Compound 12);
(S)-5-nitro-N-(4-(N-(2-oxotetrahydrofuran-3-yl)sulfamoyl)phenyl)furan-2-carboxamide (Compound 13);
(S)-5-bromo-N-(4-(N-(2-oxotetrahydrofuran-3-yl)sulfamoyl)phenyl)furan-2-carboxamide (Compound 14);
(S)-2-methyl-N-(4-(N-(2-oxotetrahydrofuran-3-yl)sulfamoyl)phenyl)furan-3-carboxamide (Compound 15);
(S)-4,5-dibromo-N-(4-(N-(2-oxotetrahydrofuran-3-yl)sulfamoyl)phenyl)furan-2-carboxamide (Compound 16);
(S)-1H—N-(4-(N-(2-oxotetrahydrofuran-3-yl)sulfamoyl)phenyl)pyrrole-2-carboxamide (Compound 17);
(S)—N-(4-(N-(2-oxotetrahydrofuran-3-yl)sulfamoyl)phenyl)pyridine-4-carboxamide (Compound 18);
(S)-6-chloro-N-(4-(N-(2-oxotetrahydrofuran-3-yl)sulfamoyl)phenyl)pyridine-3-carboxamide (Compound 19);
(S)-4-fluoro-N-(4-(N-(2-oxotetrahydrofuran-3-yl)sulfamoyl)phenyl)benzeneacetamide (Compound 20);
(S)-4-chloro-N-(4-(N-(2-oxotetrahydrofuran-3-yl)sulfamoyl)phenyl)benzeneacetamide (Compound 21);
(S)-4-bromo-N-(4-(N-(2-oxotetrahydrofuran-3-yl)sulfamoyl)phenyl)benzeneacetamide (Compound 22);
(S)-3-fluoro-N-(4-(N-(2-oxotetrahydrofuran-3-yl)sulfamoyl)phenyl)benzeneacetamide (Compound 23);
(S)-3-chloro-N-(4-(N-(2-oxotetrahydrofuran-3-yl)sulfamoyl)phenyl)benzeneacetamide (Compound 24);
(S)-3-methyl-N-(4-(N-(2-oxotetrahydrofuran-3-yl)sulfamoyl)phenyl)benzeneacetamide (Compound 25);
(S)-2-trifluoromethyl-N-(4-(N-(2-oxotetrahydrofuran-3-yl)sulfamoyl)phenyl)benzene acetamide (Compound 26);
(S)-2-fluoro-N-(4-(N-(2-oxotetrahydrofuran-3-yl)sulfamoyl)phenyl)benzeneacetamide (Compound 27);
(S)-2-chloro-N-(4-(N-(2-oxotetrahydrofuran-3-yl)sulfamyl)phenyl)benzeneacetamide (Compound 28);
(S)-2-bromo-N-(4-(N-(2-oxotetrahydrofuran-3-yl)sulfamoyl)phenyl)benzeneacetamide (Compound 29);
(S)-2-methyl-N-(4-(N-(2-oxotetrahydrofuran-3-yl)sulfamoyl)phenyl)benzeneacetamide (Compound 30);
(S)-2-nitro-N-(4-(N-(2-oxotetrahydrofuran-3-yl)sulfamoyl)phenyl)benzeneacetamide (Compound 31);
(S)-2,3-dichloro-N-(4-(N-(2-oxotetrahydrofuran-3-yl)sulfamoyl)phenyl)benzeneacetamide (Compound 32); and

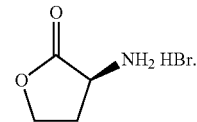

(Intermediate 1)

In the second aspect, the invention relates to a method for preparing The homoserine lactone derivative, or a racemate or optical isomer, pharmaceutically acceptable salt, solvate, or hydrate thereof according to the first aspect of the invention, comprising the following step of: reacting an intermediate of Formula 3 with acyl chloride represented by RCOCl to obtain the homoserine lactone derivative, or a racemate or optical isomer, pharmaceutically acceptable salt, solvate, or hydrate thereof according to the first aspect of the invention,

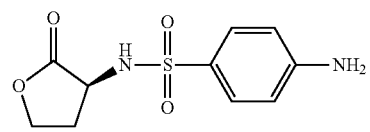

3 wherein R is as defined in the first aspect of the invention.

For the preparation method according to the second aspect of the invention, the intermediate of Formula 3 is prepared by reacting homoserine lactone hydrobromide with N-acetylsulianilyl chloride.

In an embodiment of the invention, the scheme of the preparation method is as follows:

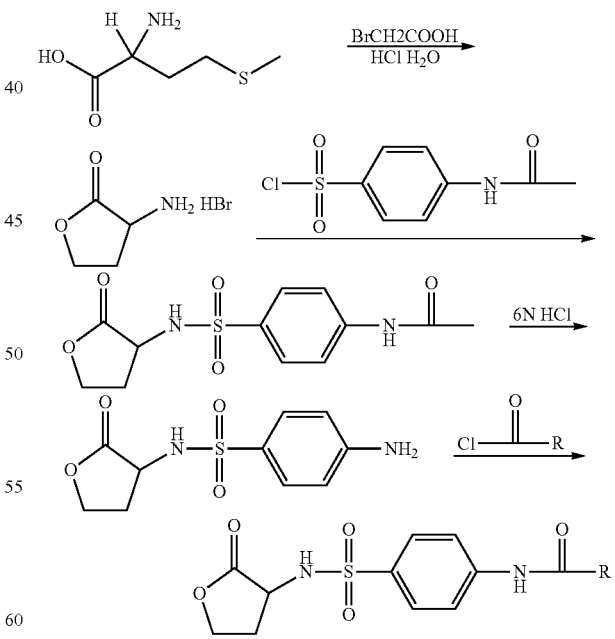

wherein R is as defined in the first aspect of the invention.

In the third aspect, the invention relates to a pharmaceutical composition, comprising the homoserine lactone derivative, or a racemate or optical isomer, pharmaceutically acceptable salt, solvate, or hydrate thereof according to the first aspect of the invention, and optionally one or more pharmaceutically acceptable carriers or excipients.

The pharmaceutical composition according to the third aspect of the invention further comprises at least one antibiotic.

For the pharmaceutical composition according to the third aspect of the invention, preferably the antibiotic includes, but is not limited to β-lactams (e.g., meropenem, cephalexin, ceftazidime, cefpirome, etc.), aminoglycosides (e.g., amikacin, streptomycin, tobramycin, isepamicin, etc.), glycopeptides (e.g., vancomycin, teicoplanin, polymyxin, etc.), macrolides (e.g., roxithromycin, clarithromycin, azithromycin, etc.), tetracyclines (e.g., doxycycline, minocycline, tigecycline, etc.), quinolones (e.g., norfloxacin, ciprofloxacin, gatifloxacin, pazufloxacin, etc.), etc.

In the fourth aspect, the invention relates to use of the homoserine lactone derivative, or a racemate or optical isomer, pharmaceutically acceptable salt, solvate, or hydrate thereof according to the first aspect of the invention in the manufacture of a medicament as a bacterial quorum-sensing regulator.

For the use according to the fourth aspect of the invention, preferably the bacterial quorum-sensing regulator may be a bacterial quorum-sensing agonist or a bacterial quorum-sensing inhibitor.

In some embodiments of the invention, a compound, or a racemate or optical isomer, pharmaceutically acceptable salt, solvate, or hydrate thereof may be used in the manufacture of a medicament as a bacterial quorum-sensing agonist, wherein the compound is selected from the group consisting of:
(S)—N-(4-(N-(2-oxotetrahydrofuran-3-yl)sulfamoyl)phenyl)furan-2-carboxamide (Compound 11);
(S)-2-fluoro-N-(4-(N-(2-oxotetrahydrofuran-3-yl)sulfamoyl)phenyl)benzeneacetamide (Compound 27); and

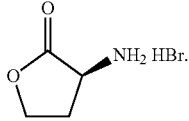

(Intermediate 1)

In some embodiments of the invention, a compound, or a racemate or optical isomer, pharmaceutically acceptable salt, solvate, or hydrate thereof may be used in the manufacture of a medicament as a bacterial quorum-sensing inhibitor, wherein the compound is selected from the group consisting of:
(S)—N-(4-(N-(2-oxotetrahydrofuran-3-yl)sulfamoyl)phenyl)thiophene-2-carboxamide (Compound 1);
(S)—N-(4-(N-(2-oxotetrahydrofuran-3-yl)sulfamoyl)phenyl)thiophene-3-carboxamide (Compound 2);
(S)-5-chloro-N-(4-(N-(2-oxotetrahydrofuran-3-yl)sulfamoyl)phenyl)thiophene-2-carboxamide (Compound 3);
(S)-5-bromo-N-(4-(N-(2-oxotetrahydrofuran-3-yl)sulfamoyl)phenyl)thiophene-2-carboxamide (Compound 4);
(S)-4-bromo-N-(4-(N-(2-oxotetrahydrofuran-3-yl)sulfamoyl)phenyl)thiophene-2-carboxamide (Compound 6);
(S)-4-methyl-N-(4-(N-(2-oxotetrahydrofuran-3-yl)sulfamoyl)phenyl)thiophene-2-carboxamide (Compound 7);
(S)-3-methyl-N-(4-(N-(2-oxotetrahydrofuran-3-yl)sulfamoyl)phenyl)thiophene-2-carboxamide (Compound 8);
(S)-3-chloro-N-(4-(N-(2-oxotetrahydrofuran-3-yl)sulfamoyl)phenyl)thiophene-2-carboxamide (Compound 9);
(S)-3-bromo-N-(4-(N-(2-oxotetrahydrofuran-3-yl)sulfamoyl)phenyl)thiophene-2-carboxamide (Compound 10);
(S)—N-(4-(N-(2-oxotetrahydrofuran-3-yl)sulfamoyl)phenyl)furan-2-carboxamide (Compound 11);
(S)—N-(4-(N-(2-oxotetrahydrofuran-3-yl)sulfamoyl)phenyl)furan-3-carboxamide (Compound 12);
(S)-5-nitro-N-(4-(N-(2-oxotetrahydrofuran-3-yl)sulfamoyl)phenyl)furan-2-carboxamide (Compound 13);
(S)-2-methyl-N-(4-(N-(2-oxotetrahydrofuran-3-yl)sulfamoyl)phenyl)furan-3-carboxamide (Compound 15);
(S)-1H—N-(4-(N-(2-oxotetrahydrofuran-3-yl)sulfamoyl)phenyl)pyrrole-2-carboxamide (Compound 17);
(S)-4-fluoro-N-(4-(N-(2-oxotetrahydrofuran-3-yl)sulfamoyl)phenyl)benzeneacetamide (Compound 20); and
(S)-4-chloro-N-(4-(N-(2-oxotetrahydrofuran-3-yl)sulfamoyl)phenyl)benzeneacetamide (Compound 21).

In the fifth aspect, the invention relates to use of the homoserine lactone derivative, or a racemate or optical isomer, pharmaceutically acceptable salt, solvate, or hydrate thereof according to the first aspect of the invention in the manufacture of a medicament for the prevention and/or treatment of a disease caused by infection of a bacterium.

For the use according to the fifth aspect of the invention, preferably the bacterium is a Gram-positive bacterium or a Gram-negative bacterium, preferably a Gram-negative bacterium.

For the use according to the fifth aspect of the invention, preferably the Gram-negative bactrium is selected from the group consisting of *E. coli, Bacillus pneumoniae, Bacillus proteus, Bacillus dysenteriae, Brucella, Haemophilus influenzae, Hemophilus parainfluenzae, Moraxella catarrhalis, Acinetobacter* spp., *Yersinia* spp., *Pasteurella* spp., *Shigella* spp., *Bordetella pertussis, Bordetella parapertussis, Vibrio Parahemolyticus, legionella pneumophila*, and *Vibrio cholera*.

For the use according to the fifth aspect of the invention, preferably the disease caused by infection of a bacterium includes, but is not limited to various diseases such as endocarditis, peritonitis, gastroenteritis, cholecystitis, cystitis, diarrhea, pyothorax, and sepsis, etc.; preferably, the disease is a disease caused by a drug-resistant strain of the bacterium, which is not sensitive to antibiotics.

In the sixth aspect, the invention relates to use of the homoserine lactone derivative, or a racemate or optical isomer, pharmaceutically acceptable salt, solvate, or hydrate thereof according to the first aspect of the invention in the manufacture of a medicament for the prevention and/or treatment of a disease caused by bacterial quorum sensing.

For the use according to the sixth aspect of the invention, preferably the disease caused by bacterial quorum sensing includes, but is not limited to various diseases caused by a Gram-negative bacterium such as *E. coli, Bacillus pneumoniae, Bacillus proteus, Bacillus dysenteriae, Brucella, Haemophilus influenzae, Hemophilus parainfluenzae, Moraxella catarrhalis, Acinetobacter* spp., *Yersinia* spp., *Pasteurella* spp., *Shigella* spp., *Bordetella pertussis, Bordetella parapertussis, Vibrio Parahemolyticus, legionella pneumophila*, and *Vibrio cholera*, wherein the diseases caused by Gram-negative bacterium include, but are not limited to endocarditis, peritonitis, gastroenteritis, cholecystitis, cystitis, diarrhea, pyothorax, sepsis, etc.; preferably, the disease is a disease caused by a drug-resistant strain of the bacterium, which is not sensitive to antibiotics.

In the seventh aspect, the invention relates to use of the homoserine lactone derivative, or a racemate or optical isomer, pharmaceutically acceptable salt, solvate, or hydrate thereof according to the first aspect of the invention as a tool drug for studying bacterial quorum sensing regulatory mechanism in vivo or in vitro.

In the eighth aspect, the invention relates to a method for preventing and/or treating a disease caused by infection of a bacterium, comprising the step of administering to a subject in need thereof a prophylactically and/or therapeutically effective amount of the homoserine lactone derivative, or a racemate or optical isomer, pharmaceutically acceptable salt, solvate, or hydrate thereof according to the first aspect of the invention.

For the method according to the eighth aspect of the invention, preferably the bacterium is a Gram-positive bacterium or a Gram-negative bacterium, preferably a Gram-negative bacterium.

For the method according to the eighth aspect of the invention, preferably the disease caused by the bacterium includes, but is not limited to various diseases caused by a Gram-negative bacterium such as *E. coli, Bacillus pneumoniae, Bacillus proteus, Bacillus dysenteriae, Brucella, Haemophilus influenzae, Hemophilus parainfluenzae, Moraxella catarrhalis, Acinetobacter* spp., *Yersinia* spp., *Pasteurella* spp., *Shigella* spp., *Bordetella pertussis, Bordetella parapertussis, Vibrio Parahemolyticus, legionella pneumophila*, and *Vibrio cholera*, wherein the diseases caused by the Gram-negative bacterium include, but are not limited to endocarditis, peritonitis, gastroenteritis, cholecystitis, cystitis, diarrhea, pyothorax, sepsis, etc.; preferably, the disease is a disease caused by a drug-resistant strain of the bacterium, which is not sensitive to antibiotics.

In the ninth aspect, the invention relates to a method for preventing and/or treating a disease caused by bacterial quorum sensing, comprising the step of administering to a subject in need thereof a prophylactically and/or therapeutically effective amount of the homoserine lactone derivative, or racemate or optical isomer, pharmaceutically acceptable salt, solvate, or hydrate thereof according to the first aspect of the invention.

For the method according to the ninth aspect of the invention, preferably the disease caused by bacterial quorum sensing includes, but is not limited to various diseases caused by a Gram-negative bacterium such as *E. coli, Bacillus pneumoniae, Bacillus proteus, Bacillus dysenteriae, Brucella, Haemophilus influenzae, Hemophilus parainfluenzae, Moraxella catarrhalis, Acinetobacter* spp., *Yersinia* spp., *Pasteurella* spp., *Shigella* spp., *Bordetella pertussis, Bordetella parapertussis, Vibrio Parahemolyticus, legionella pneumophila*, and *Vibrio cholera*, wherein the diseases caused by a Gram-negative bacterium include, but are not limited to endocarditis, peritonitis, gastroenteritis, cholecystitis, cystitis, diarrhea, pyothorax, sepsis, etc.; preferably, the disease is a disease caused by a drug-resistant strain of the bacterium, which is not sensitive to antibiotics.

The invention further relates to a method for studying bacterial quorum sensing regulatory mechanism in vivo or in vitro, comprising the step of using the homoserine lactone derivative, or racemate or optical isomer, pharmaceutically acceptable salt, solvate, or hydrate thereof according to the first aspect of the invention as a tool drug.

The invention further relates to the homoserine lactone derivative, or racemate or optical isomer, pharmaceutically acceptable salt, solvate, or hydrate thereof according to the first aspect of the invention, for use as a bacterial quorum-sensing regulator (e.g., a bacterial quorum-sensing inhibitor or agonist).

The invention further relates to the homoserine lactone derivative, or racemate or optical isomer, pharmaceutically acceptable salt, solvate, or hydrate thereof according to the first aspect of the invention, for use in the prevention and/or treatment of a disease caused by infection of a bacterium.

In some embodiments of the invention, preferably the bacterium is a Gram-positive bacterium or a Gram-negative bacterium, preferably a Gram-negative bacterium.

In some embodiments of the invention, preferably the Gram-negative bactrium is selected from the group consisting of *E. coli, Bacillus pneumoniae, Bacillus proteus, Bacillus dysenteriae, Brucella, Haemophilus influenzae, Hemophilus parainfluenzae, Moraxella catarrhalis, Acinetobacter* spp., *Yersinia* spp., *Pasteurella* spp., *Shigella* spp., *Bordetella pertussis, Bordetella parapertussis, Vibrio Parahemolyticus, legionella pneumophila*, and *Vibrio cholera*.

In some embodiments of the invention, preferably the disease caused by bacterial infection includes, but is not limited to endocarditis, peritonitis, gastroenteritis, cholecystitis, cystitis, diarrhea, pyothorax, sepsis, etc.

The invention further relates to the homoserine lactone derivative, or racemate or optical isomer, pharmaceutically acceptable salt, solvate, or hydrate thereof according to the first aspect of the invention, for use in the prevention and/or treatment of a disease caused by bacterial quorum sensing.

In some embodiments of the invention, preferably the disease caused by bacterial quorum sensing includes, but is not limited to various diseases caused by a Gram-negative bacterium such as *E. coli, Bacillus pneumoniae, Bacillus proteus, Bacillus dysenteriae, Brucella, Haemophilus influenzae, Hemophilus parainfluenzae, Moraxella catarrhalis, Acinetobacter* spp., *Yersinia* spp., *Pasteurella* spp., *Shigella* spp., *Bordetella pertussis, Bordetella parapertussis, Vibrio Parahemolyticus, legionella pneumophila*, and *Vibrio cholera*, wherein the diseases caused by the Gram-negative bacterium include, but are not limited to endocarditis, peritonitis, gastroenteritis, cholecystitis, cystitis, diarrhea, pyothorax, sepsis, etc.; preferably, the disease is a disease caused by a drug-resistant strain of the bacterium, which is not sensitive to antibiotics.

The invention further relates to the homoserine lactone derivative, or racemate or optical isomer, pharmaceutically acceptable salt, solvate, or hydrate thereof according to the first aspect of the invention, for use as a tool drug for studying bacterial quorum sensing regulatory mechanism in vivo or in vitro.

DETAILED CONTENTS OF INVENTION

The terms and phrases used in the invention have the general meanings well known by a person skilled in the art, however, if they are specifically defined herein, the meanings defined herein shall prevail.

As used herein, the term "heteroaryl" refers to a heteroaromatic group containing 5-18 members, preferably 5-14 members, and more preferably 5-10 members, including a monocyclic heteroaromatic group and a polycyclic heteroaromatic group, which is formed by fusing a monocyclic aromatic ring to one or more other aromatic rings. Heteroaryl has one or more ring heteroatoms independently selected from the group consisting of N, O and S. As used herein, the term "heteroaryl" further includes groups resulted from the fusion of aromatic ring to one or more non-aromatic rings (alicyclic ring or alicyclic hetero ring), wherein the linking group or site is on the aromatic ring. Examples of "heteroaryl" include, but are not limited to pyridyl, pyrrolyl, furyl, thienyl, pyrazolyl, imidazolyl, thiazolyl, oxazolyl, isoxazolyl, indolyl, benzofuranyl, benzimidazoyl, carbazolyl, pyridazinyl, pyrimidinyl, pyrazinyl, quinolyl, isoquinolyl, guanine group, phenothiazinyl, phenoxazolyl, etc.

As used herein, the term "halogen" has the general meanings well known in the art, and generally includes F, Cl, Br, I, as well as their isotopes, and preferably is F, Cl or Br in the invention.

As used herein, the term "$C_{1-6}$alkyl" refers to a linear, branched, or cyclic alkyl having 1-6 carbon atoms, including, but not limited to methyl, ethyl, n-propyl, isopropyl, n-butyl, sec-butyl, isobutyl, tert-butyl, pentyl, neo-pentyl, hexyl, cyclopropyl, cyclobutyl, cyclopentyl, cyclohexyl, etc.

As used herein, the groups represented by the following terms have the general meanings well known in the art: thienyl, furyl, pyrrolyl, pyridyl, benzyl, trifluoromethyl, nitro, and methyl.

As used herein, the terms "racemate" and "optical isomer" have the general meanings well known in the art.

According to the invention, the subject is a mammal, such as bovine, equine, caprid, suidae, canine, feline, rodent, and primate; wherein the particularly preferred subject is human.

According to the invention, the invention relates to a suitable pharmaceutically acceptable salt or hydrate of the compound of Formula I or an isomer thereof, wherein the pharmaceutically acceptable salt includes, but is not limited to the salts formed from the compound of Formula I with inorganic acids such as hydrochloric acid, sulphuric acid, phosphoric acid, phosphorous acid, hydrobromic acid and nitric acid, and with various organic acids such as maleic acid, malic acid, fumaric acid, succinic acid, tartaric acid, citric acid, acetic acid, lactic acid, methanesulfonic acid, p-toluene sulfonic acid, and palmitic acid. Some compounds of the invention may be crystallized or re-crystallized with water or various organic solvents. In this case, a variety of solvates may be formed. The invention includes the stoichiometric solvates, including hydrates, as well as the compound containing a variable amount of water prepared by a drying method using sublimation at low pressure.

According to the invention, the isomer of the compound of Formula I means that some compounds of the invention may be present in a form of optical isomers or tautomers. The invention includes them in all the existing forms, particularly in the forms of pure isomers. Isomers in different forms may be separated or resolved from those in other forms by various conventional means, or a certain isomer may be obtained by various conventional synthetic methods, or stereospecific or asymmetric synthetic methods. Since the compound of Formula I is used for pharmaceutical purpose, it can be understood that the compound is most preferably provided in a pure form, e.g., with a purity of at least 60%, more suitably a purity of 75%, more preferably a purity of 85%, and most preferably a purity of at least 98% (% refers to percentage by weight). Impure compounds can be applied for the preparation of the compounds in a more pure form in a pharmaceutical composition. The impure products comprise at least 1%, more suitably 5%, more preferably 10% of the compound of Formula I or a pharmaceutically acceptable derivative thereof.

According to the invention, the compounds of Formula I can be prepared by the following typical and exemplified method, comprising the following steps:

1) Methionine is added to a mixed solution of water, 2-isopropanol and glacial acetic acid and mixed homogenously, followed by an addition of bromoacetic acid. The mixture is heated to reflux for 2 h. After cooling to room temperature, the mixture is concentrated to obtain a yellow oil-like liquid. Then, a mixed solution of 2-isopropanol and toluene (1:1 V/V) is added, and the resultant mixture is concentrated under reduced pressure to obtain an orange oil-like liquid. Dioxane and concentrated hydrochloric acid are added to the oil-like liquid. The resultant mixture is heated at 50° C. for 20 min, then the heater is removed. After stirring at room temperature overnight, the mixture is placed in an ice-bath. Yellow solids are precipitated and subjected to suction filtration. The filter cake is washed with 2-isopropanol until it becomes white, to give Intermediate 1.

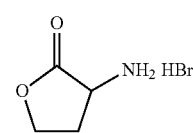

1

2) Intermediate 1 and triethanolamine are dissolved in ethanol solution. At 0° C., p-acetamidobenzene sulfonyl chloride is added in batches. After stirring at room temperature overnight, the reactants are poured into ice water, and subjected to strong agitation for 1 h. The precipitated white solids are filtrated and collected, washed with ice water, dried under vacuum, and recrystallized with ethanol, to get white solids (Intermediate 2).

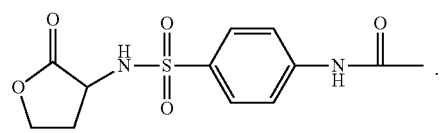

2

3) Under stirring, 6N HCl is added to an ethanol solution of Intermediate 2. After heating to reflux for 4 h, the reaction mixture is concentrated under reduced pressure. The residue is dissolved in water, and pH is adjusted to 7-8 by using ammonia water. After stirring for 1 h, the precipitated white solids are filtrated and collected, washed with ice water, dried under vacuum, and recrystallized with ethanol, to get white solids (Intermediate 3).

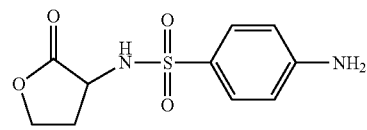

3

4) Intermediate 3 is put in a three-necked flask, and triethanolamine is added. In a 0° C. ice bath, acyl chloride (RCOCl) is added dropwisely within 10 min. The ice bath is removed, and the mixture is stirred at room temperature overnight. The reaction system is subjected to suction filtration under reduced pressure the next day, and the filtrate is washed with water. Light yellow solids are precipitated in the organic phase, the precipitated solids are filtrated and collected, and dried under vacuum to get light yellow solids (compound of Formula I).

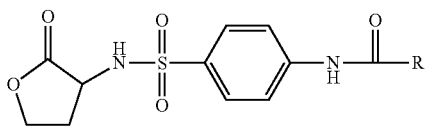

wherein R is as defined in the first aspect of the invention.

The invention further relates to a pharmaceutical composition, comprising at least one compound of Formula I and at least one pharmaceutically acceptable carrier or excipient. The compound of Formula I or a pharmaceutically acceptable salt thereof can be used alone, or in combination with a pharmaceutically acceptable carrier or excipient in the form of a pharmaceutical composition. When the compound is used in the form of a pharmaceutical composition, a suitable administration form or dosage form is generally prepared from an effective amount of the compound of Formula I, or a pharmaceutically acceptable salt or solvate thereof according to the invention, and one or more pharmaceutically acceptable carriers or excipients. The process involves mixing, granulating; compressing or dissolving the components by suitable means.

The pharmaceutical composition according to the invention may be administered by any of the following means: oral administration, spray inhalation, rectal administration, intranasal administration, vaginal administration, topical administration, parenteral administration such as subcutaneous, intravenous, intramuscular, intraperitoneal, intrathecal, intraventricular, intrasternal or intracranial injection or input, or administration by virtue of an explant reservoir, wherein oral administration, muscular injection, intraperitoneal administration, or intraventricular administration is preferred.

The pharmaceutically acceptable carrier comprised in the pharmaceutical composition of the invention includes, but is not limited to, ion exchanger, aluminum oxide, aluminum stearate, lecithin, serum protein such as human serum protein; buffer substance such as phosphate, glycerol, sorbic acid, potassium sorbate, a partial glyceride mixture of saturated plant fatty acid, water, salt, or electrolyte, such as protamine sulfate, disodium hydrogen phosphate, potassium hydrogen phosphate, sodium chloride, zinc salt, colloid silica, magnesium trisilicate, polyvinylpyrrolidone, cellulose substance, polyethylene glycol, carboxymethylcellulose sodium, polyacrylic ester, beewax, lanocerin and the like. In a pharmaceutical composition, the carrier is present in an amount of 1%~98% by weight, generally of about 80% by weight. For the convenience of use, local anesthetics, preservatives, buffers and the like may be directly dissolved in the carrier.

Oral formulations such as oral tablets and capsules may comprise excipients such as binders, e.g., syrup, arabic gum, sorbitol, *Astragalus* gummifer, or polyvinylpyrrolidone; fillers, such as lactose, sucrose, corn starch, calcium phosphate, sorbitol, and aminoacetic acid; lubricants, such as magnesium stearate, talc, polyethylene glycol, and silica; disintegrants, such as potato starch; or acceptable lubrication-enhancing agents, such as sodium lauryl sulfate. The tablet may be coated by methods well known in pharmaceutics.

The pharmaceutical composition of the invention in an oral liquid form may be prepared into a suspension of water and oil, a solution, an emulsion, a syrup or an elixir, or into a dry product, which is supplemented with water or other suitable medium prior to use. The liquid formulation may comprise conventional additives such as suspending agent, sorbitol, methyl cellulose, glucose syrup, gel, hydroxyethyl cellulose, carboxymethyl cellulose, aluminum stearate gel, hydrogenated edible fat, emulsifier such as lecithin, sorbitan monooleate, gum arabic; or non-aqueous carrier (which may comprise edible oil), such as almond oil, fat such as glycerol, ethylene glycol or ethanol; preservative, such as methyl or propyl parahydroxybenzoate, sorbic acid. If necessary, flavoring agents or coloring agents may be added. Suppositories may comprise conventional suppository bases, such as cocoa butter or other glycerides. For parenteral administration, a liquid dosage form is generally prepared from a compound and at least one sterilized or aseptic carrier. The optimal carrier is water. Depending on the selected carrier and the concentration of a drug, the compound may be dissolved in the carrier or be prepared into a suspension solution. When preparing an injection, the compound is dissolved in water first, and packaged into a seal bottle or an ampoule after filtration and sterilization. When topically administered to skin, the compounds of the invention may be prepared in a suitable form of ointments, lotions or creams, wherein the active ingredient is suspended or dissolved in one or more carriers. The carriers for use in ointment preparations include, but are not limited to: mineral oil, liquid paraffin, white vaseline, propylene glycol, polyethylene oxide, polypropylene oxide, emulsifying wax and water; carriers for use in lotions and creams include, but are not limited to: mineral oil, sorbitan monostearate, Tween 60, hexadecylester wax, hexadecane aromatic alcohol, 2-octyl dodecanol, benzyl alcohol and water. Depending on the administration route, the composition may comprises 0.1 wt %, more suitably 10-60 wt % of active ingredient. However, when the composition is in a unit dosage form, each unit best comprises 50-500 mg active ingredient. Depending on the administration route and the administration frequency, a therapeutic dose suitable for an adult, for example, is 100-3000 mg per day, such as 1500 mg per day.

It has to be realized that the best administration dose and interval of the compound of Formula I depend on the severity of a disease or disorder, the properties of the compound, and the conditions such as administration form, route and site, and the particular mammal to be treated. The best administration dose can be determined by a physician in clinic.

Beneficial Technical Effects of the Invention

The present invention provides a series of new bacterial quorum-sensing regulators, which deprive pathogenic bacteria of pathogenic ability by regulating the expression of virulence genes in the pathogenic bacteria, without interfering with normal physiological functions of cells, thus are regarded as a new direction for the development of antibacterials. Among them, bacterial quorum-sensing inhibitors can be used in combination with antibiotics to prevent and/or treat various diseases caused by a Gram-negative bacterium such as endocarditis, peritonitis, gastroenteritis, cholecystitis, cystitis, diarrhea, pyothorax, and sepsis; and are particularly suitable for use in the prevention and/or treatment of a disease caused by a drug-resistant Gram-negative bacterium not sensitive to existing antibiotics.

SPECIFIC MODES FOR CARRYING OUT THE INVENTION

The invention is further described by the following intermediates and examples. However, it should be understood that these intermediates and examples are only used to describe the invention more detailedly, and should not be understood as restricting the invention in any manner.

The invention describes the materials and experimental methods used in the experiments generally and/or in detail. Although many materials and methods used to achieve the purpose of the invention are well known in the art, the invention still describes them as detailedly as possible. A person skilled in the art knows that unless otherwise specified, the materials and methods used in the invention are well known in the art.

In the following examples, the melting points of the compounds were measured by YRT-4 type melting point apparatus, wherein the temperature was not calibrated. The specific rotatory power was measured by Polaar 3005 type Accuracy Automatic Polarimeter from OA Company. 1H-NMR spectra were measured by Bruker ARX 400 type NMR spectrometer. FAB mass spectra were measured by Zabspect High Resolution mass spectrometer.

Preparation of Intermediates

[Preparation of Intermediate 1] (L)-homoserine lactone hydrobromide

Intermediate 1

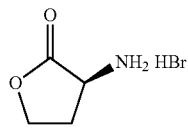

20.0 g (134 mmol) L-methionine was added to a mixed solution of 80 ml water, 80 ml 2-isopropanol and 32 ml glacial acetic acid and mixed homogenously, followed by an addition of 18.8 g (134 mmol) bromoacetic acid. The mixture was heated to reflux for 2 h. After cooling to room temperature, the mixture was concentrated to obtain a yellow oil-like liquid. A mixed solution of 2-isopropanol and toluene (1:1 V/V, 70 ml) was added to the obtained liquid. The resultant mixture was mixed and concentrated to give an orange oil-like liquid. 56 ml dioxane and 28 ml concentrated hydrochloric acid were added to the oil-like liquid. The resultant mixture was heated at 50° C. for 15 min, then the heater was removed. After stirring at room temperature overnight, the reaction system was placed in an ice-bath for 4 h. light yellow solids were precipitated and suction filtration was performed. The filter cake was washed with 2-isopropanol until it became white, to get 10.9 g product (Intermediate 1), with a yield of 45%.

1H-NMR (400 MHz, D2O) δ ppm: 8.76 (s, 3H), 4.46 (t, 1H, J=8.0 Hz, J=7.6 Hz), 4.35-4.31 (m, 2H), 2.56-2.51 (m, 1H), 2.30-2.27 (m, 1H); EI-MS (m/z): 102.1 [M+H]+; m.p. 220-224° C.; $[\alpha]_D^{25}$=−24.2 (c=0.1, H2O).

Preparation of Intermediate 2

(s)-N-(4-(N-(2-oxotetrahydrofuran-3-yl)sulfamoyl)phenyl)acetamide

Intermediate 2

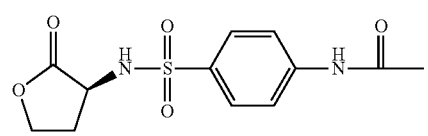

16.8 g (72 mmol) p-acetamidobenzene sulfonyl chloride was added in batches to 120 mL ethanol solution of 10.9 g (60 mmol) (L)-homoserine lactone hydrobromide (Intermediate 1) and 25.5 mL (120 mmol) triethanolamine at 0° C. After stirring at room temperature overnight, the reactants were poured into ice water (200 mL) the next day and were stirred for 1 h. The precipitated white solids were filtrated and collected, washed with ice water, dried under vacuum, and recrystallized with ethanol, to get 12 g white solids (Intermediate 2), with a yield of 67%.

1H-NMR (400 MHz, DMSO) δ ppm: 10.33 (s, 1H), 8.16 (d, 1H, J=8.0 Hz), 7.75 (s, 4H), 4.34-4.30 (m, 1H), 4.21 (m, 1H), 4.08 (m, 1H), 2.08-2.06 (m, 4H), 1.80 (m, 1H); EI-MS (m/z): 299.34 [M+H]+; m.p. 174-176° C.

Preparation of Intermediate 3

(s)-4-amino-N-(2-oxotetrahydrofuran-3-yl)benzenesulfonamide

Intermediate 3

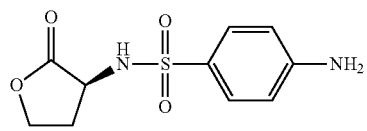

Under stirring, 20 mL 6N HCl was added to 40 mL ethanol solution of 10 g (33 mmol) (s)-N-(4-(N-(2-oxotetrahydrofuran-3-yl)sulfamoyl)phenyl)acetamide. After heating to reflux for 4 h, the reaction mixture was concentrated under reduced pressure. The residue was dissolved in water, and pH was adjusted to 7-8 by using 1N ammonia water. After stirring for 1 h, the precipitated white solids were filtrated and collected, washed with ice water, dried under vacuum, and recrystallized with ethanol, to get 5.2 g white solids (Intermediate 3), with a yield of 57%.

1H-NMR (400 MHz, DMSO) δ ppm: 7.72 (d, 1H, J=9.2 Hz), 7.45 (d, 2H, J=8.4 Hz), 6.61 (d, 2H, J=8.8 Hz), 5.95 (m, 2H), 4.21 (m, 2H), 4.09 (m, 1H), 2.06 (m, 1H), 1.78 (m, 1H); EI-MS: m/z=256.4 [M+H]+; m.p. 162-165° C.

EXAMPLES

Example 1

(s)-N-(4-(N-(2-oxotetrahydrofuran-3-yl)sulfamoyl)phenyl)thiophene-2-carboxamide (Compound 1)

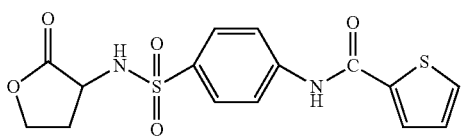

Compound 1

0.52 g (2.03 mmol) (s)-4-amino-N-(2-oxotetrahydrofuran-3-yl)benzenesulfonamide (Intermediate 3) was put in a three-necked flask containing 15 ml anhydrous dichloromethane, and 0.41 g (4.06 mmol) triethanolamine was added. In a 0° C. ice bath, 0.36 g (2.44 mmol) thiophene-2-carbonyl chloride is slowly added dropwisely within 10 min. The ice bath was removed, and the mixture was stirred at room temperature overnight. The reaction system was subjected to suction filtration under reduced pressure the next day, and the filtrate was washed with water. Light yellow solids were precipitated in the organic phase, and the precipitated solids were subjected to suck filtration under reduced pressure, and dried under vacuum to get 0.44 g light yellow solids (Compound 1), with a yield of 60%.

1H-NMR (400 MHz, DMSO) δ ppm: 10.57 (s, 1H), 8.25 (1H, d, J=8.0 Hz), 8.22 (d, 1H, J=8.0 Hz), 8.07 (d, 1H, J=8.0 Hz), 7.93 (m, 3H), 7.82 (d, 2H, J=8.0 Hz), 7.26 (d, 1H, J=8.0 Hz), 4.37 (m, 1H), 4.23 (m, 1H), 4.11 (m, 1H), 2.14 (m, 1H), 1.84 (m, 1H); EI-MS: m/z=366.9 [M+H]+; m.p. 114-119° C.

Example 2

(s)-N-(4-(N-(2-oxotetrahydrofuran-3-yl)sulfamoyl)phenyl)thiophene-3-carboxamide (Compound 2)

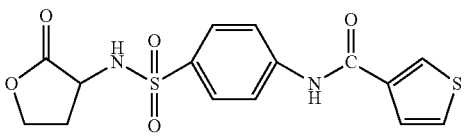

Compound 2

Intermediate 3 and thiophene-3-carbonyl chloride were used as raw materials, and operations were performed as described in Example 1, to get khaki solid product (Compound 2).

1H-NMR (400 MHz, DMSO) δ ppm: 10.38 (s, 1H), 8.42 (1H, s), 8.20 (d, 1H, J=8.0 Hz), 7.96 (d, 2H, J=8.0 Hz), 7.82 (m, 2H), 7.68 (d, 2H, J=8.0 Hz), 4.37 (m, 1H), 4.23 (m, 1H), 4.11 (m, 1H), 2.14 (m, 1H), 1.83 (m, 1H); EI-MS: m/z=367.0 [M+H]+; m.p. 212-216° C.

Example 3

(s)-5-chloro-N-(4-(N-(2-oxotetrahydrofuran-3-yl)sulfamoyl)phenyl)thiophene-2-carb oxamide (Compound 3)

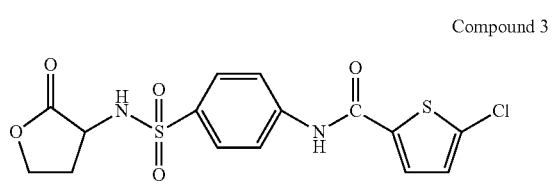 [SMILES: O=C(Nc1ccc(S(=O)(=O)NC2CCOC2=O)cc1)c1ccc(Br)s1]

Compound 3

Intermediate 3 and 5-chloro-thiophene-2-carbonyl chloride were used as raw materials, and operations were performed as described in Example 1, to get orange solid product (Compound 3).

1H-NMR (400 MHz, DMSO) δ ppm: 10.64 (s, 1H), 8.21 (d, 1H, J=8.0 Hz), 7.94 (m, 3H), 7.82 (d, 2H, J=8.0 Hz), 7.32 (s, 1H), 4.37 (m, 1H), 4.22 (m, 1H), 4.10 (m, 1H), 2.14 (m, 1H), 1.83 (m, 1H); EI-MS: m/z=401.1 [M+H]+; m.p. 243-249° C.

Example 4

(s)-5-bromo-N-(4-(N-(2-oxotetrahydrofuran-3-yl)sulfamoyl)phenyl)thiophene-2-carb oxamide (Compound 4)

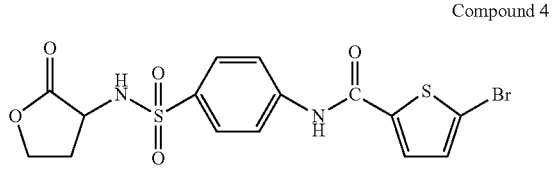

Compound 4

Intermediate 3 and 5-bromo-thiophene-2-carbonyl chloride were used as raw materials, and operations were performed as described in Example 1, to get orange solid product (Compound 4).

1H-NMR (400 MHz, DMSO) δ ppm: 10.63 (s, 1H), 8.21 (d, 1H, J=8.0 Hz), 7.91 (m, 3H), 7.83 (d, 2H, J=8.0 Hz), 7.40 (s, 1H), 4.36 (m, 1H), 4.22 (m, 1H), 4.10 (m, 1H), 2.13 (m, 1H), 1.83 (m, 1H); EI-MS: m/z=445.0 [M+H]+; m.p. 197-199° C.

Example 5

(s)-5-nitro-N-(4-(N-(2-oxotetrahydrofuran-3-yl)sulfamoyl)phenyl)thiophene-2-carboxamide (Compound 5)

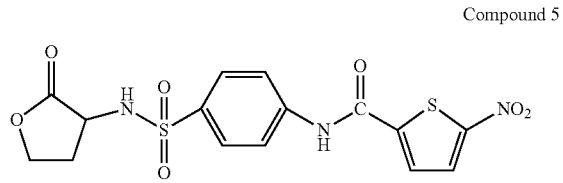 [SMILES: O=C(Nc1ccc(S(=O)(=O)NC2CCOC2=O)cc1)c1ccc([N+](=O)[O-])s1]

Compound 5

Intermediate 3 and 5-nitro-thiophene-2-carbonyl chloride were used as raw materials, and operations were performed as described in Example 1, to get white solid product (Compound 5).

1H-NMR (400 MHz, DMSO) δ ppm: 10.96 (s, 1H), 8.23 (d, 2H, J=8.0 Hz), 8.10 (d, 1H, J=8.0 Hz), 7.93 (m, 4H), 4.36 (m, 1H), 4.21 (m, 1H), 4.09 (m, 1H), 2.13 (m, 1H), 1.83 (m, 1H); EI-MS: m/z=434.2 [M+Na]+; m.p. 208-220° C.

Example 6

(s)-4-bromo-N-(4-(N-(2-oxotetrahydrofuran-3-yl)sulfamoyl)phenyl)thiophene-2-carboxamide (Compound 6)

Compound 6

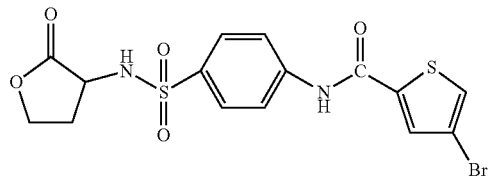

Intermediate 3 and 4-bromo-thiophene-2-carbonyl chloride were used as raw materials, and Operations were performed as they were in Example 1, to get orange solid product (Compound 6).

1H-NMR (400 MHz, DMSO) δ ppm: 10.66 (s, 1H), 8.24 (d, 1H, J=8.0 Hz), 8.12 (d, 2H, J=8.0 Hz), 7.94 (m, 2H), 7.86 (m, 2H), 4.38 (m, 1H), 4.23 (m, 1H), 4.11 (m, 1H), 2.14 (m, 1H), 1.84 (m, 1H); EI-MS: m/z=445.0[M+H]+; m.p. 197-203° C.

Example 7

(s)-4-methyl-N-(4-(N-(2-oxotetrahydrofuran-3-yl)sulfamoyl)phenyl)thiophene-2-carboxamide (Compound 7)

Compound 7

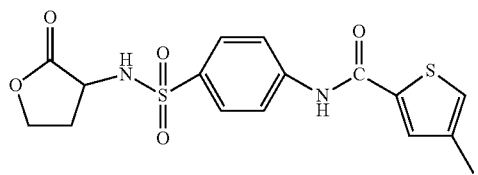

Intermediate 3 and 4-methyl-thiophene-2-carbonyl chloride were used as raw materials, and operations were performed as described in Example 1, to get light-yellow solid product (Compound 7).

1H-NMR (400 MHz, DMSO) δ ppm: 10.50 (s, 1H), 8.23 (d, 1H, J=8.0 Hz), 7.94 (m, 3H), 7.81 (d, 2H, J=8.0 Hz), 7.51 (d, 1H, J=8.0 Hz), 4.37 (m, 1H), 4.23 (m, 1H), 4.11 (m, 1H), 2.14 (m, 1H), 1.83 (m, 1H); EI-MS (m/z): 381.1[M+H]+; m.p. 187-188° C.

Example 8

(s)-3-methyl-N-(4-(N-(2-oxotetrahydrofuran-3-yl)sulfamoyl)phenyl)thiophene-2-carboxamide (Compound 8)

Compound 8

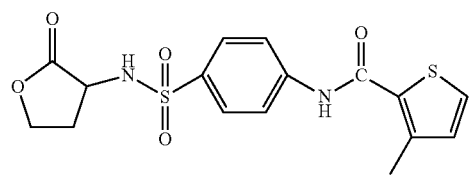

Intermediate 3 and 3-methyl-thiophene-2-carbonyl chloride were used as raw materials, and operations were performed as described in Example 1, to get white solid product (Compound 8).

1H-NMR (400 MHz, DMSO) δ ppm: 10.36 (s, 1H), 8.23 (d, 1H, J=8.0 Hz), 7.88 (d, 2H, J=8.0 Hz), 7.79 (d, 2H, J=8.0 Hz), 7.72 (m, 1H), 7.06 (d, 1H, J=8.0 Hz), 4.36 (m, 1H), 4.23 (m, 1H), 4.11 (m, 1H), 2.14 (m, 1H), 1.83 (m, 1H); EI-MS: m/z=381.0[M+H]+; m.p. 176-178° C.

Example 9

(s)-3-chloro-N-(4-(N-(2-oxotetrahydrofuran-3-yl)sulfamoyl)phenyl)thiophene-2-carboxamide (Compound 9)

Compound 9

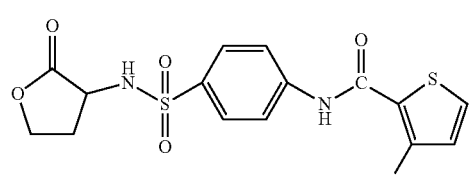

Intermediate 3 and 3-chloro-thiophene-2-carbonyl chloride were used as raw materials, and operations were performed as described in Example 1, to get light-yellow solid product (Compound 9).

1H-NMR (400 MHz, DMSO) δ ppm: 10.63 (s, 1H), 8.23 (d, 1H, J=8.0 Hz), 7.96 (m, 1H), 7.87 (d, 2H, J=8.0 Hz), 7.82 (d, 2H, J=8.0 Hz), 7.24 (d, 1H, J=8.0 Hz), 4.37 (m, 1H), 4.23 (m, 1H), 4.11 (m, 1H), 2.13 (m, 1H), 1.83 (m, 1H); =401.3 [M+H]+; m.p. 219-221° C.

Example 10

(s)-3-bromo-N-(4-(N-(2-oxotetrahydrofuran-3-yl)sulfamoyl)phenyl)thiophene-2-carboxamide (Compound 10)

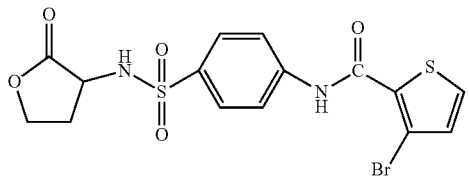

Compound 10

Intermediate 3 and 3-chloro-thiophene-2-carbonyl chloride were used as raw materials, and operations were performed as described in Example 1, to get light-yellow solid product (Compound 10).

1H-NMR (400 MHz, DMSO) δ ppm: 10.71 (s, 1H), 8.24 (d, 1H, J=8.0 Hz), 7.92 (m, 1H), 7.87 (d, 2H, J=8.0 Hz), 7.83 (d, 2H, J=8.0 Hz), 7.27 (d, 1H, J=8.0 Hz), 4.37 (m, 1H), 4.23 (m, 1H), 4.11 (m, 1H), 2.13 (m, 1H), 1.83 (m, 1H); EI-MS: m/z=444.9[M+H]+; m.p. 151-154° C.

Example 11

(s)-N-(4-(N-(2-oxotetrahydrofuran-3-yl)sulfamoyl)phenyl)furan-2-carboxamide (Compound 11)

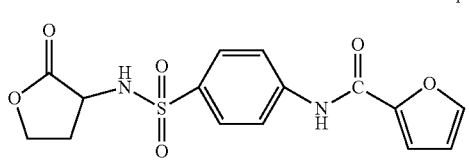

Compound 11

Intermediate 3 and furan-2-carbonyl chloride were used as raw materials, and operations were performed as described in Example 1, to get orange solid product (Compound 11).

1H-NMR (400 MHz, DMSO) δ ppm: 10.49 (s, 1H), 8.18 (d, 1H, J=8.0 Hz), 7.96 (m, 3H), 7.82 (d, 2H, J=8.0 Hz), 7.40 (d, 1H, J=8.0 Hz), 6.72 (d, 1H, J=8.0 Hz), 4.36 (m, 1H), 4.23 (m, 1H), 4.11 (m, 1H), 2.17 (m, 1H), 1.86 (m, 1H); EI-MS: m/z=351.1[M+H]+; m.p. 195-196° C.

Example 12

(s)-N-(4-(N-(2-oxotetrahydrofuran-3-yl)sulfamoyl)phenyl)furan-3-carboxamide (Compound 12)

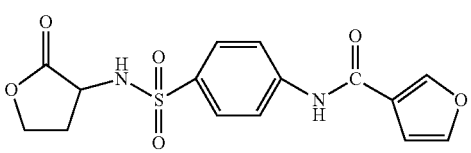

Compound 12

Intermediate 3 and furan-3-carbonyl chloride were used as raw materials, and operations were performed as described in Example 1, to get light-yellow solid product (Compound 12).

1H-NMR (400 MHz, DMSO) δ ppm: 10.28 (s, 1H), 8.44 (s, 1H), 8.21 (d, 1H, J=8.0 Hz), 7.92 (m, 5H), 7.02 (d, 1H, J=8.0 Hz), 4.36 (m, 1H), 4.23 (m, 1H), 4.10 (m, 1H), 2.13 (m, 1H), 1.82 (m, 1H); EI-MS: m/z=351.1[M+H]+; m.p. 202-209° C.

Example 13

(s)-5-nitro-N-(4-(N-(2-oxotetrahydrofuran-3-yl)sulfamoyl)phenyl)furan-2-carboxamide (Compound 13)

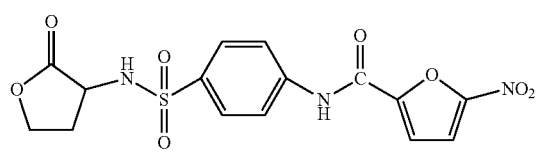

Compound 13

Intermediate 3 and 5-nitro-furan-2-carbonyl chloride were used as raw materials, and operations were performed as described in Example 1, to get light-yellow solid product (Compound 13).

1H-NMR (400 MHz, DMSO) δ ppm: 10.97 (s, 1H), 8.26 (d, 1H, J=8.0 Hz), 7.95 (d, 2H, J=8.0 Hz), 7.85 (m, 3H), 7.71 (d, 1H, J=8.0 Hz), 4.37 (m, 1H), 4.23 (m, 1H), 4.10 (m, 1H), 2.13 (m, 1H), 1.86 (m, 1H); EI-MS: m/z=396.0[M+H]+; m.p. 113-120° C.

Example 14

(s)-5-bromo-N-(4-(N-(2-oxotetrahydrofuran-3-yl)sulfamoyl)phenyl)furan-2-carboxamide (Compound 14)

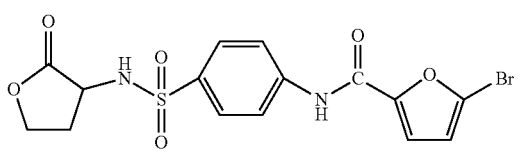

Compound 14

Intermediate 3 and 5-bromo-furan-2-carbonyl chloride were used as raw materials, and operations were performed as described in Example 1, to get light-yellow solid product (Compound 14).

1H-NMR (400 MHz, DMSO) δ ppm: 10.56 (s, 1H), 8.24 (d, 1H, J=8.0 Hz), 7.94 (d, 2H, J=8.0 Hz), 7.81 (d, 2H, J=8.0 Hz), 7.45 (d, 1H, J=8.0 Hz), 6.87 (d, 1H, J=8.0 Hz), 4.36 (m, 1H), 4.23 (m, 1H), 4.10 (m, 1H), 2.13 (m, 1H), 1.83 (m, 1H); EI-MS: m/z=453.1[M+Na]+; m.p. 190-196° C.

Example 15

(s)-2-methyl-N-(4-(N-(2-oxotetrahydrofuran-3-yl)sulfamoyl)phenyl)furan-3-carboxamide (Compound 15)

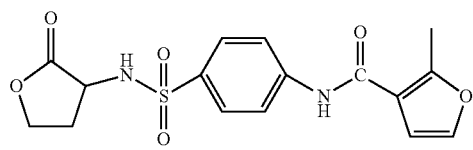

Compound 15

Intermediate 3 and 2-methyl-furan-3-carbonyl chloride were used as raw materials, and operations were performed as described in Example 1, to get light-yellow solid product (Compound 15).

1H-NMR (400 MHz, DMSO) δ ppm: 10.05 (s, 1H), 8.21 (d, 1H, J=8.0 Hz), 7.94 (d, 2H, J=8.0 Hz), 7.79 (d, 2H, J=8.0 Hz), 7.63 (d, 1H, J=8.0 Hz), 7.09 (d, 1H, J=8.0 Hz), 4.36 (m, 1H), 4.23 (m, 1H), 4.11 (m, 1H), 2.53 (s, 3H), 2.13 (m, 1H), 1.83 (m, 1H); EI-MS: m/z=365.0[M+H]+; m.p. 185-187° C.

Example 16

(s)-4,5-dibromo-N-(4-(N-(2-oxotetrahydrofuran-3-yl)sulfamoyl)phenyl)furan-2-carboxamide (Compound 16)

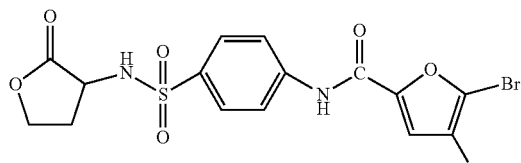

Compound 16

Intermediate 3 and 4,5-dibromo-furan-2-carbonyl chloride were used as raw materials, and operations were performed as described in Example 1, to get light-yellow solid product (Compound 16).

1H-NMR (400 MHz, DMSO) δ ppm: 10.66 (s, 1H), 8.23 (d, 1H, J=8.0 Hz), 7.94 (d, 2H, J=8.0 Hz), 7.82 (d, 2H, J=8.0 Hz), 7.69 (d, 1H, J=8.0, Hz), 4.36 (m, 1H), 4.23 (m, 1H), 4.11 (m, 1H), 2.14 (m, 1H), 1.85 (m, 1H); EI-MS: m/z=529.0[M+Na]+; m.p. 217-219° C.

Example 17

(s)-1H—N-(4-(N-(2-oxotetrahydrofuran-3-yl)sulfamoyl)phenyl)pyrrole-2-carboxamide (Compound 17)

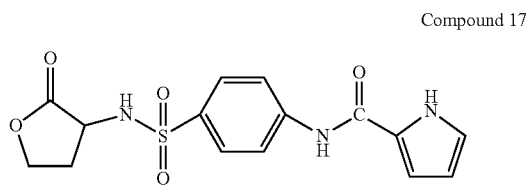 [SMILES: O=C(Nc1ccc(S(=O)(=O)NC2CCOC2=O)cc1)c1ccc[nH]1]

Compound 17

Intermediate 3 and pyrrole-2-carbonyl chloride were used as raw materials, and operations were performed as described in Example 1, to get light-yellow solid product (Compound 17).

1H-NMR (400 MHz, DMSO) δ ppm: 11.79 (d, 1H, J=8.0 Hz), 10.10 (s, 1H), 8.17 (d, 1H, J=8.0 Hz), 7.95 (d, 2H, J=8.0 Hz), 7.80 (d, 2H, J=8.0 Hz), 7.12 (d, 1H, J=8.0 Hz), 7.02 (d, 1H, J=8.0 Hz), 6.20 (d, 1H, J=8.0 Hz), 4.36 (m, 1H), 4.23 (m, 1H), 4.11 (m, 1H), 2.13 (m, 1H), 1.83 (m, 1H); EI-MS: m/z=365.0[M+H]+; m.p. 170-174° C.

Example 18

(s)-N-(4-(N-(2-oxotetrahydrofuran-3-yl)sulfamoyl)phenyl)pyridine-4-carboxamide (7-19) (Compound 18)

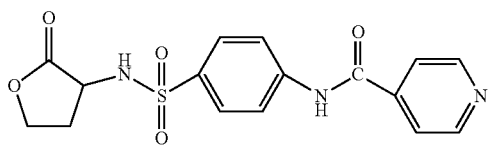

Compound 18

Intermediate 3 and pyridine-4-carbonyl chloride were used as raw materials, and operations were performed as described in Example 1, to get white solid product (Compound 18).

1H-NMR (400 MHz, DMSO) δ ppm: 10.86 (s, 1H), 8.81 (m, 2H), 8.23 (d, 1H, J=8.0 Hz), 7.97 (d, 2H, J=8.0 Hz), 7.86 (m, 4H), 4.36 (m, 1H), 4.23 (m, 1H), 4.11 (m, 1H), 2.14 (m, 1H), 1.83 (m, 1H); EI-MS: m/z=362.1[M+H]+; m.p. 174-185° C.

Example 19

(s)-6-chloro-N-(4-(N-(2-oxotetrahydrofuran-3-yl)sulfamoyl)phenyl)pyridine-3-carboxamide (Compound 19)

Compound 19

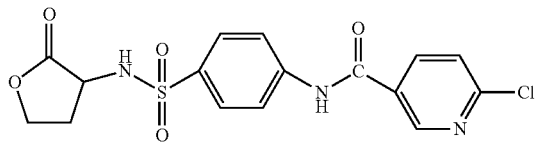

Intermediate 3 and 6-chloro-pyridine-3-carbonyl chloride were used as raw materials, and operations were performed as described in Example 1, to get light-yellow solid product (Compound 19).

1H-NMR (400 MHz, DMSO) δ ppm: 10.85 (s, 1H), 8.96 (d, 1H, J=8.0 Hz), 8.36 (d, 1H, J=8.0 Hz), 8.25 (d, 1H, J=8.0 Hz), 7.96 (d, 2H, J=8.0 Hz), 7.85 (d, 2H, J=8.0 Hz), 7.76 (d, 1H, J=8.0 Hz), 4.38 (m, 1H), 4.23 (m, 1H), 4.09 (m, 1H), 2.14 (m, 1H), 1.83 (m, 1H); EI-MS: m/z=396.1[M+H]+; m.p. 190-191° C.

Example 20

(S)-4-fluoro-N-(4-(N-(2-oxotetrahydrofuran-3-yl)sulfamoyl)phenyl)benzeneacetamide (Compound 20)

Compound 20

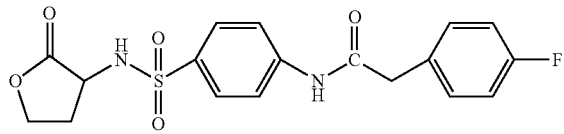

Intermediate 3 and 4-fluoro-phenylacetyl chloride were used as raw materials, and operations were performed as described in Example 1, to get light-yellow solid product (Compound 20).

¹H-NMR (400 MHz, DMSO) δ ppm: 10.58 (s, 1H), 8.18 (d, 1H, J=8.0 Hz), 7.77 (m, 4H), 7.36 (d, 2H, J=8.0 Hz), 7.17 (dd, 2H, J=8.0 Hz), 4.34 (m, 1H), 4.20 (m, 1H), 4.09 (m, 1H), 3.69 (s, 2H), 2.09, (m, 1H), 1.80 (m, 1H); EI-MS: m/z=393.1[M+H]+; m.p. 187-194° C.

Example 21

(S)-4-chloro-N-(4-(N-(2-oxotetrahydrofuran-3-yl)sulfamoyl)phenyl)benzeneacetamide (Compound 21)

Compound 21

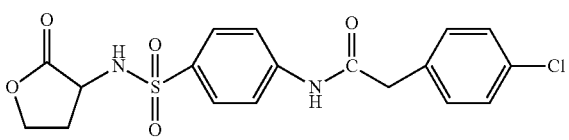

Intermediate 3 and 4-chloro-phenylacetyl chloride were used as raw materials, and operations were performed as described in Example 1, to get white solid product (Compound 21).

¹H-NMR (400 MHz, DMSO) δ ppm: 10.57 (s, 1H), 8.16 (d, 1H, J=8.0 Hz), 7.76 (m, 4H), 7.37 (m, 4H), 4.33 (m, 1H), 4.21 (m, 1H), 4.09 (m, 1H), 3.70 (s, 2H), 2.10 (m, 1H), 1.80 (m, 1H); EI-MS: m/z=409.2[M+H]+; m.p. 169-180° C.

Example 22

(S)-4-bromo-N-(4-(N-(2-oxotetrahydrofuran-3-yl)sulfamoyl)phenyl)benzeneacetamide (Compound 22)

Compound 22

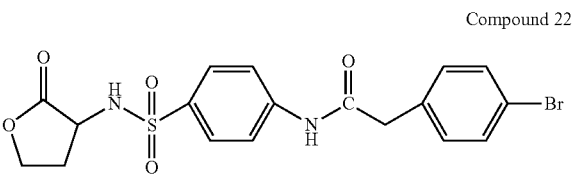 [SMILES: O=C(Cc1ccc(Br)cc1)Nc1ccc(S(=O)(=O)NC2CCOC2=O)cc1]

Intermediate 3 and 4-bromo-phenylacetyl chloride were used as raw materials, and operations were performed as described in Example 1, to get light-yellow solid product (Compound 22).

¹H-NMR (400 MHz, DMSO) δ ppm: 10.57 (s, 1H), 8.16 (d, 1H, J=8.0 Hz), 7.77 (m, 4H), 7.52 (d, 2H, J=8.0 Hz), 7.29 (d, 2H, J=8.0 Hz), 4.33 (m, 1H), 4.20 (m, 1H), 4.09 (m, 1H), 3.68 (s, 2H), 2.10 (m, 1H), 1.80 (m, 1H); EI-MS: m/z=453.3 [M+H]+; m.p. 184-186° C.

Example 23

(S)-3-fluoro-N-(4-(N-(2-oxotetrahydrofuran-3-yl)sulfamoyl)phenyl)benzeneacetamide (Compound 23)

Compound 23

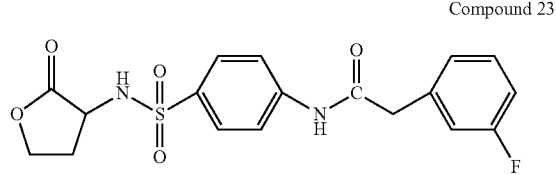 [SMILES: O=C(Cc1cccc(F)c1)Nc1ccc(S(=O)(=O)NC2CCOC2=O)cc1]

Intermediate 3 and 3-fluoro-phenylacetyl chloride were used as raw materials, and operations were performed as described in Example 1, to get light-yellow solid product (Compound 23).

¹H-NMR (400 MHz, DMSO) δ ppm: 10.58 (s, 1H), 8.16 (d, 1H, J=8.0 Hz), 7.76 (m, 4H), 7.37 (m, 1H), 7.18 (m, 3H), 4.32 (m, 1H), 4.21 (m, 1H), 4.09 (m, 1H), 3.73 (s, 2H), 2.10 (m, 1H), 1.80 (m, 1H); EI-MS: m/z=393.2[M+H]+; m.p. 175-177° C.

Example 24

(S)-3-chloro-N-(4-(N-(2-oxotetrahydrofuran-3-yl)sulfamoyl)phenyl)benzeneacetamide (Compound 24)

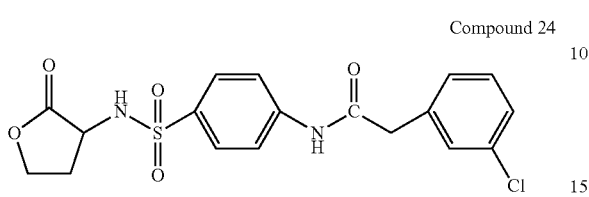

Compound 24

Intermediate 3 and 3-chloro-phenylacetyl chloride were used as raw materials, and operations were performed as described in Example 1, to get white solid product (Compound 24).

$^1$H-NMR (400 MHz, DMSO) δ ppm: 10.59 (s, 1H), 8.18 (d, 1H, J=8.0 Hz), 7.76 (m, 4H), 7.37 (m, 4H), 4.33 (m, 1H), 4.21 (m, 1H), 4.09 (m, 1H), 3.73 (s, 2H), 2.10 (m, 1H), 1.80 (m, 1H); EI-MS: m/z=409.1[M+H]+; m.p. 188-190° C.

Example 25

(S)-3-methyl-N-(4-(N-(2-oxotetrahydrofuran-3-yl)sulfamoyl)phenyl)benzeneacetamide (Compound 25)

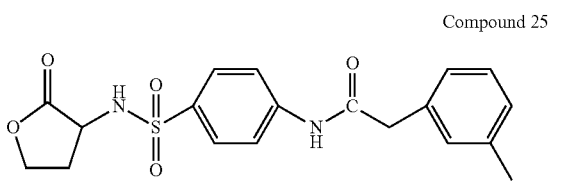 [SMILES: Cc1cccc(CC(=O)Nc2ccc(S(=O)(=O)NC3CCOC3=O)cc2)c1]

Compound 25

Intermediate 3 and 3-methyl-phenylacetyl chloride were used as raw materials, and operations were performed as described in Example 1, to get white solid product (Compound 25).

$^1$H-NMR (400 MHz, DMSO) δ ppm: 10.58 (s, 1H), 8.18 (d, 1H, J=8.0 Hz), 7.78 (m, 4H), 7.16 (m, 4H), 4.33 (m, 1H), 4.20 (m, 1H), 4.08 (m, 1H), 3.73 (s, 2H), 2.11 (m, 1H), 1.80 (m, 1H); EI-MS: m/z=389.1[M+H]+; m.p. 191-193° C.

Example 26

(S)-2-trifluoromethyl-N-(4-(N-(2-oxotetrahydrofuran-3-yl)sulfamoyl)phenyl)benzene acetamide (Compound 26)

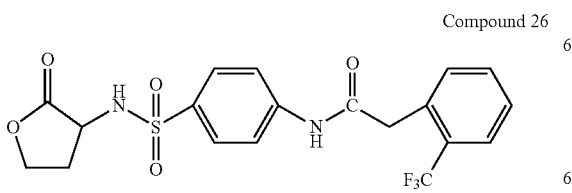

Compound 26

Intermediate 3 and 2-trifluoromethyl-phenylacetyl chloride were used as raw materials, and operations were performed as described in Example 1, to get white solid product (Compound 26).

$^1$H-NMR (400 MHz, DMSO) δ ppm: 10.63 (s, 1H), 8.18 (d, 1H, J=8.0 Hz), 7.74 (m, 6H), 7.53 (m, 2H), 4.33 (m, 1H), 4.22 (m, 1H), 4.08 (m, 1H), 3.98 (s, 2H), 2.10 (m, 1H), 1.81 (m, 1H); EI-MS: m/z=443.3[M+H]+; m.p. 197-198° C.

Example 27

(S)-2-fluoro-N-(4-(N-(2-oxotetrahydrofuran-3-yl)sulfamoyl)phenyl)benzeneacetamide (Compound 27)

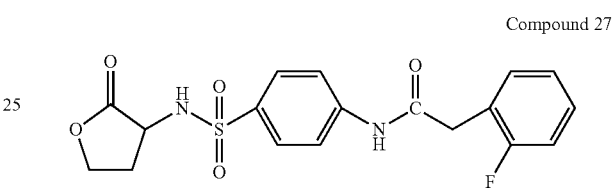

Compound 27

Intermediate 3 and 2-fluoro-phenylacetyl chloride were used as raw materials, and operations were performed as described in Example 1, to get white solid product (Compound 27).

$^1$H-NMR (400 MHz, DMSO) δ ppm: 10.62 (s, 1H), 8.17 (d, 1H, J=8.0 Hz), 7.76 (m, 4H), 7.19 (m, 4H), 4.32 (m, 1H), 4.21 (m, 1H), 4.06 (m, 1H), 3.78 (s, 2H), 2.11 (m, 1H), 1.80 (m, 1H); EI-MS: m/z=393.3[M+H]+; m.p. 185-186° C.

Example 28

(S)-2-chloro-N-(4-(N-(2-oxotetrahydrofuran-3-yl)sulfamoyl)phenyl)benzeneacetamide (Compound 28)

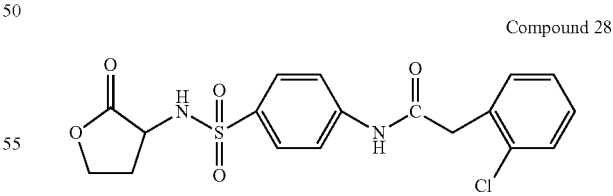

Compound 28

Intermediate 3 and 2-chloro-phenylacetyl chloride were used as raw materials, and operations were performed as described in Example 1, to get white solid product (Compound 28).

$^1$H-NMR (400 MHz, DMSO) δ ppm: 10.64 (s, 1H), 8.18 (d, 1H, J=8.0 Hz), 7.78 (m, 4H), 7.44 (m, 4H), 4.33 (m, 1H), 4.21 (m, 1H), 4.08 (m, 1H), 3.89 (s, 2H), 2.11 (m, 1H), 1.81 (m, 1H); EI-MS: m/z=409.2[M+H]+; m.p. 223-228° C.

Example 29

(S)-2-bromo-N-(4-(N-(2-oxotetrahydrofuran-3-yl)sulfamoyl)phenyl)benzeneacetamide (Compound 29)

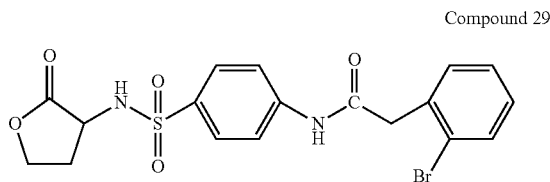 [SMILES: O=C(Cc1ccccc1Br)Nc1ccc(S(=O)(=O)NC2CCOC2=O)cc1]

Compound 29

Intermediate 3 and 2-bromo-phenylacetyl chloride were used as raw materials, and operations were performed as described in Example 1, to get white solid product (Compound 29).
$^1$H-NMR (400 MHz, DMSO) δ ppm: 10.65 (s, 1H), 8.18 (d, 1H, J=8.0 Hz), 7.79 (m, 4H), 7.62 (d, 1H, J=8.0 Hz), 7.42 (m, 2H), 7.22 (m, 1H), 4.34 (m, 1H), 4.22 (m, 1H), 4.08 (m, 1H), 3.91 (s, 2H), 2.13 (m, 1H), 1.83 (m, 1H); EI-MS: m/z=475.2[M+Na]+; m.p. 227-229° C.

Example 30

(S)-2-methyl-N-(4-(N-(2-oxotetrahydrofuran-3-yl)sulfamoyl)phenyl)benzeneacetamide (Compound 30)

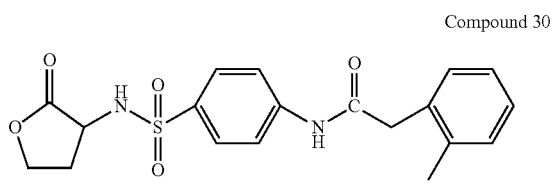 [SMILES: Cc1ccccc1CC(=O)Nc1ccc(S(=O)(=O)NC2CCOC2=O)cc1]

Compound 30

Intermediate 3 and 2-methyl-phenylacetyl chloride were used as raw materials, and operations were performed as described in Example 1, to get white solid product (Compound 30).
$^1$H-NMR (400 MHz, DMSO) δ ppm: 10.56 (s, 1H), 8.17 (d, 1H, J=8.0 Hz), 7.78 (m, 4H), 7.16 (m, 4H), 4.35 (m, 1H), 4.21 (m, 1H), 4.08 (m, 1H), 3.73 (s, 2H), 2.10 (m, 1H), 1.81 (m, 1H); EI-MS: m/z=389.2[M+H]+; m.p. 208-210° C.

Example 31

(S)-2-nitro-N-(4-(N-(2-oxotetrahydrofuran-3-yl)sulfamoyl)phenyl)benzeneacetamide (Compound 31)

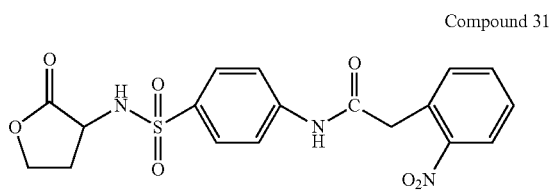

Compound 31

Intermediate 3 and 2-nitro-phenylacetyl chloride were used as raw materials, and operations were performed as described in Example 1, to get orange solid product (Compound 31).
$^1$H-NMR (400 MHz, DMSO) δ ppm: 0.66 (s, 1H), 8.18 (d, 1H, J=8.0 Hz), 8.08 (d, 1H, J=8.0 Hz), 7.75 (m, 5H), 7.59 (m, 2H), 4.34 (m, 1H), 4.21 (m, 1H), 4.18 (s, 2H), 4.08 (m, 1H), 2.11 (m, 1H), 1.81 (m, 1H); EI-MS: m/z=420.4[M+H]+; m.p. 216-219° C.

Example 32

(S)-2,3-dichloro-N-(4-(N-(2-oxotetrahydrofuran-3-yl)sulfamoyl)phenyl)benzeneacetamide (Compound 32)

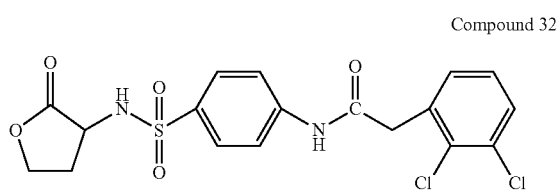 [SMILES: O=C(Cc1cccc(Cl)c1Cl)Nc1ccc(S(=O)(=O)NC2CCOC2=O)cc1]

Compound 32

Intermediate 3 and 2,3-dichloro-phenylacetyl chloride were used as raw materials, and operations were performed as described in Example 1, to get light-yellow solid product (Compound 32).
$^1$H-NMR (400 MHz, DMSO) δ ppm: 10.67 (s, 1H), 8.17 (d, 1H, J=8.0 Hz), 7.77 (m, 4H), 7.56 (d, 1H, J=8.0 Hz), 7.36 (m, 2H), 4.34 (m, 1H), 4.20 (m, 1H), 4.08 (m, 1H), 3.97 (s, 2H), 2.11 (m, 1H), 1.81 (m, 1H); EI-MS: m/z=443.3[M+H]+; m.p. 230-237° C.

[Experimental Example] Evaluation of Activity of the Bacterial Quorum-Sensing Regulators of the Invention The activity of the bacterial quorum-sensing regulators of the invention may be measured by the following methods.
1. Method for Preliminary Screening
1.1 Preparation work: compounds to be tested (Compounds 1-32 prepared in Example 1-32 and Intermediates 1-3) were weighed and then separately dissolved in 200 µl DMSO (dimethyl sulfoxide) to prepare a solution at a concentration of 0.065M. 5.0 mg inducer, N-hexanoyl homoserine lactone ($C_6$—HSL, purchased from Sigma Company) was weighed and dissolved in 200 µl DMSO (at a concentration of 0.125M), the compounds and the inducer were all stored at 4° C. for further use. *C. violaceum* CV026 (donated by Professor McLean J C from Texas State University, the bacterium is the Tn-5 mutant of the wild type *Chromobacterium violaceum* ATCC31532; see Latifi, A., et al., Mol. Microbiol, 17, 333-343(1995) and Winson, M. K., et al., Proc. Natl. Acad. Sci. USA, 92, 9427-9431(1995)) was cultured under shaking in a shaker at 30° C., 200 rpm.
1.2 Method for preliminary screening of compounds having agonistic activity: 400 µl *C. violaceum* CV026 was added to 5 ml melted semi-solid LB culture medium (1% tryptone, 1% NaCl, and 0.5% yeast extract), and mixed homogeneously; the mixed culture medium was poured into a solid LB plate; when the mixed culture medium was solidified on the plate; 1 μl sample of the dissolved compound to be tested (Compounds 1-32 in Examples 1-32) was spotted on the plate; when the sample was dried in air, the plate was put in a 30° C. oven upside down and cultured for a period of 16-18 h. The agonistic activity of the compound was determined depending on whether purple strain was induced for C. violaceum CV026 on LB plate as well as the density of purple strain.

1.3 Method for preliminary screening of compounds having inhibitory activity: the inducer $C_6$-HSL was diluted gradiently to 1000 times by means of 2-fold dilution; 15 μl of the diluted inducer and 400 μl C. violaceum CV026 in exponential phase were mixed homogeneously and then added to a 5 ml melted semi-solid LB culture medium; the mixture of inducer, C. violaceum, and semi-solid LB culture medium were poured onto a solid LB plate; when the mixture was solidified on the plate, 1 μl sample of the dissolved compound to be tested (Compounds 1-32 in Examples 1-32 and Intermediates 1-3) was spotted on the plate; when the sample was dried in air, the plate was put in a 30° C. oven upside down and was cultured for a period of 16-18 h. The inhibitory activity of a compound was preliminary determined depending on the size of the white circle appeared after C. violaceum CV026 was inhibited on LB plate.

It is found, after preliminary screening, that 17 compounds according to the invention have bacterial quorum sensing regulatory activity, and the screening result was shown in Table 1.

2. Measurement of $IC_{50}$ of Compounds Having an Inhibitory Effect on C. violaceum Quorum Sensing 2.1 The wells of a 12-well plate were marked as initial concentration group, 2, 4, 8, 16, 32, 64, 128, and 256 fold diluted group, DMSO group, and a blank control group from left to right and from up to bottom, respectively.

2.2 The monoclonal C. violaceum CV026 grew on LB solid plate was cultured to exponential phase in a 5 ml fresh LB liquid culture medium, and 50 μl was then taken for seeding in a 5 ml LB culture medium, and cultured until the optical density OD value was about 1.0. The culture was then mixed homogeneously with LB culture medium at a ratio of 1:9 (at an OD of about 0.15), and added to a 12-well plate in an amount of 2 ml/well.

2.3 The compounds having quorum sensing inhibitory activity in preliminarily screening were dissolved in DMSO (at a concentration of 0.065M), respectively, and then 10 μl was taken into 10 μl DMSO solution for 2-fold dilution, and so on. Each compound was gradiently diluted to a highest fold of 256 (gradient dilution of 2, 4, 8, 16, 32, 64, 128, 256 fold).

2.4 To each well, 15 μl 1000-fold diluted inducer $C_6$-HSL (initial concentration of 0.125M) and 8 μl compound solution at each diluted gradient was added; to the DMSO group, 8 μl DMSO was added; to the blank control group, 8 μl LB culture medium was added. Finally, it was ensured that 2 ml culture in each of the 12-well plate was mixed homogeneously.

2.5 The 12-well plate was placed in a 30° C. shaker at 130 rpm and cultured for 10-12 h.

2.6 After the culture was finished, 1 ml culture was taken from each well and put in a 1.5 ml EP tube and then centrifuged at 12000 rpm for 10 mins. The supernatant of the culture was sucked out, and 500 μl DMSO was added to each EP tube to dissolve the purple pigment in the culture. After the pigment was completely dissolved, centrifugation was performed at 12000 rpm for 10 mins. 200 μl supernatant pigment was put in a 96-well culture plate, and measured for absorbance value at 585 nm by a Microplate Reader. The absorbance value and the corresponding concentration were plotted to get the $IC_{50}$ value. The specific results were shown in Table 2.

TABLE 1

Preliminary screening result of bacterial quorum sensing regulatory activity

| Compound No. | Regulatory activity | Compound No. | Regulatory activity |
|---|---|---|---|
| Intermediate 1 | + | Intermediate 2 | − |
| 1 | − | 2 | − |
| 3 | − | 4 | − |
| 6 | − | 7 | − |
| 8 | − | 9 | − |
| 10 | − | 11 | ± |
| 12 | − | 13 | − |
| 15 | − | 17 | − |
| 20 | − | 21 | − |
| 27 | + | | |

In Table 1, "+" represents that a compound has bacterial quorum sensing agonistic activity, "−" represents that a compound has bacterial quorum sensing inhibitory activity, and "±" represents that a compound has both agonistic and inhibitory activity on the bacterial quorum sensing.

TABLE 2

$IC_{50}$ value (μM) of compounds having bacterial quorum sensing inhibitory activity

| Compound No. | $IC_{50}$ |
|---|---|
| 8 | 69.22 ± 1.42 |
| 9 | 9.19 ± 0.34 |
| 10 | 13.51 ± 0.54 |

Although the embodiments of the invention are described in detail, a person skilled in the art would understand that according to all the already disclosed teachings, these details can be modified and replaced, and these alterations all fall in the protection scope of the invention. The scope of the invention is defined by the claims and any equivalent thereof.

What is claimed is:

1. A homoserine lactone compound of Formula I, or a racemate or optical isomer, pharmaceutically acceptable salt, solvate, or hydrate thereof,

B.

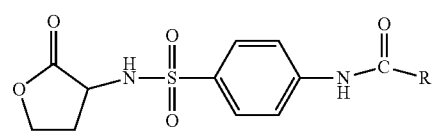

I wherein, R is a group selected from heteroaryl and benzyl, optionally the group is mono-substituted or multi-substituted by a substituent selected from a group consisting of: halogen, trifluoromethyl, nitro, and $C_{1-6}$ alkyl.

2. The homoserine lactone compound, or a racemate or optical isomer, pharmaceutically acceptable salt, solvate, or hydrate thereof according to claim 1, wherein R is a group selected from thienyl, furyl, pyrrolyl, pyridyl and benzyl, optionally the group is mono-substituted or multi-substituted by a substituent selected from the group consisting of halogen, trifluoromethyl, nitro, and $C_{1-6}$ alkyl.

3. The homoserine lactone compound, or a racemate or optical isomer, pharmaceutically acceptable salt, solvate, or hydrate thereof according to claim 1, wherein R is selected from the group consisting of thienyl, chlorothienyl, bromothienyl, nitrothienyl, methylthienyl, furyl, nitrofuryl, bromofuryl, methylfuryl, dibromofuryl, pyrrolyl, pyridyl, chloropyridyl, fluorobenzyl, chlorobenzyl, bromobenzyl, methylbenzyl, nitrobenzyl, trifluoromethylbenzyl, and dichlorobenzyl.

4. The homoserine lactone compound of Formula I, or a racemate or optical isomer, pharmaceutically acceptable salt, solvate, or hydrate thereof according to claim 1, wherein the homoserine lactone compound is selected from:
- (S)—N-(4-(N-(2-oxotetrahydrofuran-3-yl)sulfamoyl) phenyl)thiophene-2-carboxamide (Compound 1);
- (S)—N-(4-(N-(2-oxotetrahydrofuran-3-yl)sulfamoyl) phenyl)thiophene-3-carboxamide (Compound 2);
- (S)-5-chloro-N-(4-(N-(2-oxotetrahydrofuran-3-yl)sulfamoyl)phenyl)thiophene-2-carboxamide (Compound 3);
- (S)-5-bromo-N-(4-(N-(2-oxotetrahydrofuran-3-yl)sulfamoyl)phenyl)thiophene-2-carboxamide (Compound 4);
- (S)-5-nitro-N-(4-(N-(2-oxotetrahydrofuran-3-yl)sulfamoyl)phenyl)thiophene-2-carboxamide (Compound 5);
- (S)-4-bromo-N-(4-(N-(2-oxotetrahydrofuran-3-yl)sulfamoyl)phenyl)thiophene-2-carboxamide (Compound 6);
- (S)-4-methyl-N-(4-(N-(2-oxotetrahydrofuran-3-yl)sulfamoyl)phenyl)thiophene-2-carboxamide (Compound 7);
- (S)-3-methyl-N-(4-(N-(2-oxotetrahydrofuran-3-yl)sulfamoyl)phenyl)thiophene-2-carboxamide (Compound 8);
- (S)-3-chloro-N-(4-(N-(2-oxotetrahydrofuran-3-yl)sulfamoyl)phenyl)thiophene-2-carboxamide (Compound 9);
- (S)-3-bromo-N-(4-(N-(2-oxotetrahydrofuran-3-yl)sulfamoyl)phenyl)thiophene-2-carboxamide (Compound 10);
- (S)—N-(4-(N-(2-oxotetrahydrofuran-3-yl)sulfamoyl) phenyl)furan-2-carboxamide (Compound 11);
- (S)—N-(4-(N-(2-oxotetrahydrofuran-3-yl)sulfamoyl) phenyl)furan-3-carboxamide (Compound 12);
- (S)-5-nitro-N-(4-(N-(2-oxotetrahydrofuran-3-yl)sulfamoyl)phenyl)furan-2-carboxamide (Compound 13);
- (S)-5-bromo-N-(4-(N-(2-oxotetrahydrofuran-3-yl)sulfamoyl)phenyl)furan-2-carboxamide (Compound 14);
- (S)-2-methyl-N-(4-(N-(2-oxotetrahydrofuran-3-yl)sulfamoyl)phenyl)furan-3-carboxamide (Compound 15);
- (S)-4,5-dibromo-N-(4-(N-(2-oxotetrahydrofuran-3-yl) sulfamoyl)phenyl)furan-2-carboxamide (Compound 16);
- (S)-1H—N-(4-(N-(2-oxotetrahydrofuran-3-yl)sulfamoyl) phenyl)pyrrole-2-carboxamide (Compound 17);
- (S)—N-(4-(N-(2-oxotetrahydrofuran-3-yl)sulfamoyl) phenyl)pyridine-4-carboxamide (Compound 18);
- (S)-6-chloro-N-(4-(N-(2-oxotetrahydrofuran-3-yl)sulfamoyl)phenyl)pyridine-3-carboxamide (Compound 19);
- (S)-4-fluoro-N-(4-(N-(2-oxotetrahydrofuran-3-yl)sulfamoyl)phenyl)benzeneacetamide (Compound 20);
- (S)-4-chloro-N-(4-(N-(2-oxotetrahydrofuran-3-yl)sulfamoyl)phenyl)benzeneacetamide (Compound 21);
- (S)-4-bromo-N-(4-(N-(2-oxotetrahydrofuran-3-yl)sulfamoyl)phenyl)benzeneacetamide (Compound 22);
- (S)-3-fluoro-N-(4-(N-(2-oxotetrahydrofuran-3-yl)sulfamoyl)phenyl)benzeneacetamide (Compound 23);
- (S)-3-chloro-N-(4-(N-(2-oxotetrahydrofuran-3-yl)sulfamoyl)phenyl)benzeneacetamide (Compound 24);
- (S)-3-methyl-N-(4-(N-(2-oxotetrahydrofuran-3-yl)sulfamoyl)phenyl)benzeneacetamide (Compound 25);
- (S)-2-trifluoromethyl-N-(4-(N-(2-oxotetrahydrofuran-3-yl)sulfamoyl)phenyl) benzeneacetamide (Compound 26);
- (S)-2-fluoro-N-(4-(N-(2-oxotetrahydrofuran-3-yl)sulfamoyl)phenyl)benzeneacetamide (Compound 27);
- (S)-2-chloro-N-(4-(N-(2-oxotetrahydrofuran-3-yl)sulfamoyl)phenyl)benzeneacetamide (Compound 28);
- (S)-2-bromo-N-(4-(N-(2-oxotetrahydrofuran-3-yl)sulfamoyl)phenyl)benzeneacetamide (Compound 29);
- (S)-2-methyl-N-(4-(N-(2-oxotetrahydrofuran-3-yl)sulfamoyl)phenyl)benzeneacetamide (Compound 30);
- (S)-2-nitro-N-(4-(N-(2-oxotetrahydrofuran-3-yl)sulfamoyl)phenyl)benzeneacetamide (Compound 31); and
- (S)-2,3-dichloro-N-(4-(N-(2-oxotetrahydrofuran-3-yl) sulfamoyl)phenyl)benzeneacetamide (Compound 32).

5. The homoserine lactone compound, or a racemate or optical isomer, pharmaceutically acceptable salt, solvate, or hydrate thereof according to claim 1, for use as a bacterial quorum-sensing regulator.

6. The homoserine lactone compound, or a racemate or optical isomer, pharmaceutically acceptable salt, solvate, or hydrate thereof according to claim 1, wherein R is a group selected from heteroaryl and benzyl, optionally the group is di-substituted or tri-substituted by a substituent selected from a group consisting of: halogen, trifluoromethyl, nitro, and $C_{1-6}$ alkyl.

7. The homoserine lactone compound, or a racemate or optical isomer, pharmaceutically acceptable salt, solvate, or hydrate thereof according to claim 2, wherein, R is a group selected from thienyl, furyl, pyrrolyl, pyridyl and benzyl, optionally the group is di-substituted or tri-substituted by a substituent selected from the group consisting of halogen, trifluoromethyl, nitro, and $C_{1-6}$ alkyl.

8. A method for preparing the homoserine lactone compound of Formula I, or a racemate or optical isomer, pharmaceutically acceptable salt, solvate, or hydrate thereof according to claim 1, comprising the following steps of: reacting an intermediate of Formula 3 with acyl chloride represented by RCOCl, to obtain the homoserine lactone compound, or a racemate or optical isomer, pharmaceutically acceptable salt, solvate, or hydrate thereof according to claim 1,

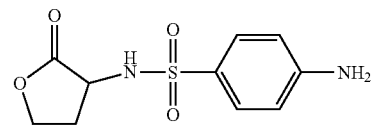

3 wherein R is as defined in claim 1.

9. The method according to claim 8, wherein the intermediate of Formula 3 is prepared by reacting homoserine lactone hydrobromide with acetylsulianilyl chloride.

10. A pharmaceutical composition comprising the homoserine lactone compound, or a racemate or optical isomer, pharmaceutically acceptable salt, solvate, or hydrate thereof according to claim 1, and optionally one or more pharmaceutically acceptable carriers or excipients.

11. The pharmaceutical composition according to claim 10, further comprising at least one antibiotic.

12. A method for preventing and/or treating a disease caused by infection of a bacterium, comprising the step of administering to a subject in need thereof a prophylactically and/or therapeutically effective amount of the homoserine lactone compound, or a racemate or optical isomer, pharmaceutically acceptable salt, solvate, or hydrate thereof according to claim 1, wherein the disease is selected from the group consisting of endocarditis, peritonitis, gastroenteritis, cholecystitis, cystitis, diarrhea, pyothorax, or sepsis.

13. The method according to claim 12, wherein the bacterium is a Gram-positive bacterium or a Gram-negative bacterium.

14. The method according to claim 13, wherein the Gram-negative bacterium is selected from the group consisting of *E. coli, Bacillus pneumoniae, Bacillus proteus, Bacillus dysenteriae, Brucella, Haemophilus influenzae, Hemophilus parainfluenzae, Moraxella catarrhalis, Acinetobacter* spp., *Yersinia* spp., *Pasteurella* spp., *Shigella* spp., *Bordetella pertussis, Bordetella parapertussis, Vibrio Parahemolyticus, legionella pneumophila*, and *Vibrio cholera*.

15. The method according to claim 12, wherein the disease is a disease caused by a drug-resistant strain of the bacterium, which is not sensitive to antibiotics.

16. A method for preventing and/or treating a disease caused by bacterial quorum sensing, comprising the step of administering to a subject in need thereof a prophylactically and/or therapeutically effective amount of the homoserine lactone compound, or a racemate or optical isomer, pharmaceutically acceptable salt, solvate, or hydrate thereof according to claim 1, wherein the disease is selected from the group consisting of endocarditis, peritonitis, gastroenteritis, cholecystitis, cystitis, diarrhea, pyothorax, and sepsis.

17. The method according to claim 16, wherein the disease caused by bacterial quorum sensing is a disease caused by a Gram-negative bacterium.

18. The method according to claim 17, wherein the Gram-negative bacterium is selected from the group consisting of *E. coli, Bacillus pneumoniae, Bacillus proteus, Bacillus dysenteriae, Brucella, Haemophilus influenzae, Hemophilus parainfluenzae, Moraxella catarrhalis, Acinetobacter* spp., *Yersinia* spp., *Pasteurella* spp., *Shigella* spp., *Bordetella pertussis, Bordetella parapertussis, Vibrio Parahemolyticus, legionella pneumophila*, and *Vibrio cholera*.

19. The method according to claim 17, wherein the disease is a disease caused by a drug-resistant strain of the bacterium, which is not sensitive to antibiotics.

20. A method for studying bacterial quorum sensing regulatory mechanism in vivo or in vitro, comprising using the homoserine lactone compound, or a racemate or optical isomer, pharmaceutically acceptable salt, solvate, or hydrate thereof according to claim 1, as a tool drug.

* * * * *